United States Patent
Okada et al.

(10) Patent No.: US 10,835,214 B2
(45) Date of Patent: Nov. 17, 2020

(54) SUPPORT BODY, BODY FLUID COLLECTION SET, AND BODY FLUID COLLECTION METHOD

(71) Applicant: Sysmex Corporation, Kobe (JP)

(72) Inventors: Seiki Okada, Kobe (JP); Yasuhito Ohnishi, Kobe (JP)

(73) Assignee: SYSMEX CORPORATION, Hyogo (JP)

(*) Notice: Subject to any disclaimer, the term of this patent is extended or adjusted under 35 U.S.C. 154(b) by 52 days.

(21) Appl. No.: 15/689,872

(22) Filed: Aug. 29, 2017

(65) Prior Publication Data

US 2018/0055492 A1 Mar. 1, 2018

(30) Foreign Application Priority Data

Aug. 30, 2016 (JP) ................. 2016-167528

(51) Int. Cl.
*B65D 81/00* (2006.01)
*A61B 10/00* (2006.01)
(Continued)

(52) U.S. Cl.
CPC ...... *A61B 10/0064* (2013.01); *A61B 5/14532* (2013.01); *A61B 5/150022* (2013.01);
(Continued)

(58) Field of Classification Search
CPC .......... A61B 10/0064; A61B 5/150969; A61B 5/150022; A61B 2560/0412; A61B 2560/045
See application file for complete search history.

(56) References Cited

U.S. PATENT DOCUMENTS

| 5,443,080 A | 8/1995 | D'Angelo et al. |
| 5,944,662 A * | 8/1999 | Schoendorfer .... A61B 5/14521 600/362 |

(Continued)

FOREIGN PATENT DOCUMENTS

| JP | 3144460 U | 8/2008 |
| JP | 2011-050733 A | 3/2011 |

(Continued)

OTHER PUBLICATIONS

Extended European search report dated Nov. 20, 2019 in a counterpart European application No. 19188322.2.

(Continued)

*Primary Examiner* — Christian Jang
(74) *Attorney, Agent, or Firm* — Brinks Gilson & Lione

(57) ABSTRACT

Disclosed are a support body, a body fluid collection set, and a body fluid collection method that can easily support a body fluid collection sheet even by a non-physician. The support body 1 includes a first sheet 10 having an adhesive surface 12 for adhering the body fluid collection sheet 30, and a second sheet 20 adhered to the first sheet 10. The adhesive surface 12 of the first sheet 10 is adhered to the body fluid collection sheet 30 so that the first sheet 10 is separated from the skin 40 and the body fluid collection sheet 30 is peeled off from the skin 40. Thereafter, the second sheet 20 is superposed on the adhesive surface 12, and the body fluid collection sheet 30 is supported on the support body 1.

14 Claims, 17 Drawing Sheets

First Embodiment

(51) Int. Cl.
*A61B 5/15* (2006.01)
*A61B 5/145* (2006.01)

(52) U.S. Cl.
CPC .. *A61B 5/150969* (2013.01); *A61B 2010/008* (2013.01); *A61B 2560/045* (2013.01); *A61B 2560/0412* (2013.01)

(56) References Cited

U.S. PATENT DOCUMENTS

2008/0300508 A1   12/2008   Tomer
2013/0018279 A1   1/2013    Plante et al.

FOREIGN PATENT DOCUMENTS

JP    2014-163845 A   9/2014
WO    WO 95/24859 A1   9/1995
WO    WO 99/02967 A1   1/1999

OTHER PUBLICATIONS

Japanese Office Action dated Feb. 4, 2020 in a counterpart Japanese patent application No. 2016-167528.
Communication pursuant to Article 94(3) EPC dated Sep. 21, 2020 in a counterpart European patent application No. 19188322.2.

* cited by examiner

First Embodiment

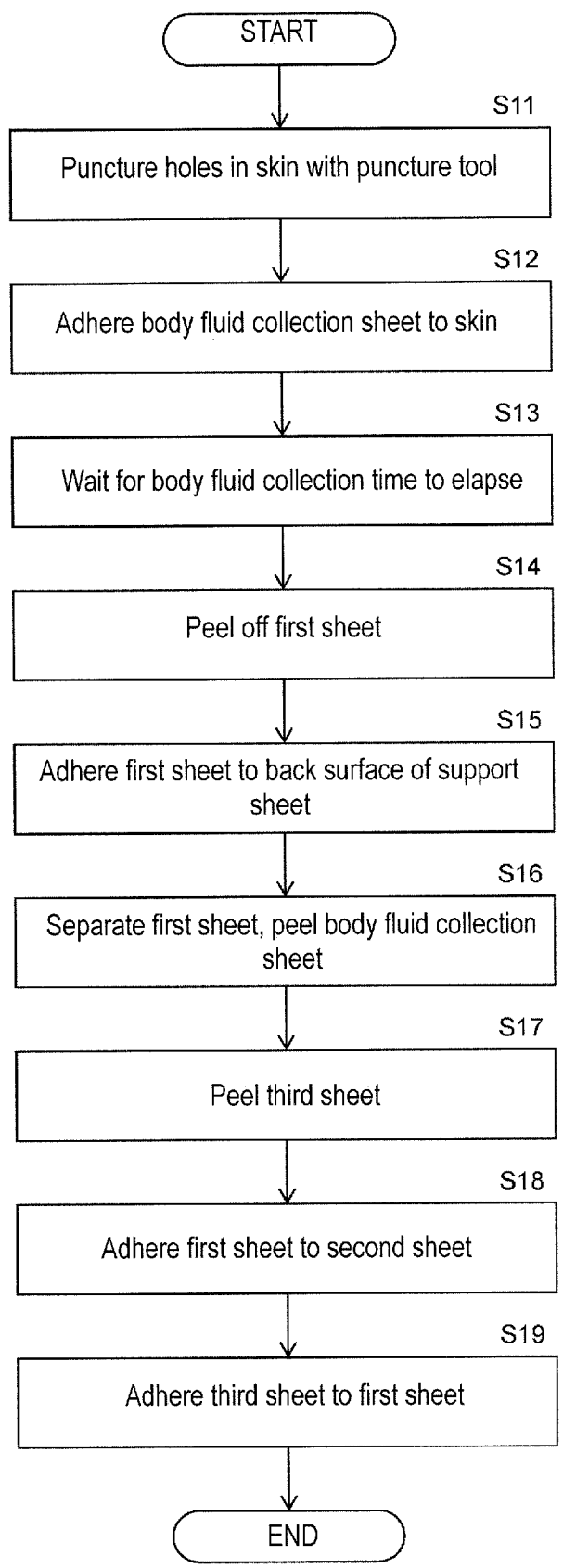

Second Embodiment

SUPPORT BODY, BODY FLUID COLLECTION SET, AND BODY FLUID COLLECTION METHOD

RELATED APPLICATIONS

This application claims priority from prior Japanese Patent Application No. 2016-167528, filed on Aug. 30, 2016, entitled "Support Body, Body Fluid Collection Set, and Body Fluid Collection Method", the entire contents of which are incorporated herein by reference.

BACKGROUND OF THE INVENTION

1. Field of the Invention

The present invention relates to The present invention relates to a support body for supporting a body fluid collection sheet, a body fluid collection set for collection of body fluids, and a body fluid collection method for collecting body fluids.

2. Description of the Related Art

Conventional body fluid collection sheets for percutaneously collecting bodily fluids such as interstitial fluid and perspiration by a body fluid collecting body made of a water retentive gel are known. The body fluid collection sheet is configured by a body fluid collection body and an adhesive sheet for adhering the body fluid collection body to the skin. The body fluid collection sheet is affixed to the skin for a predetermined time in a state wherein the body fluid collection body is in close contact with the skin. In the case of collecting interstitial fluid from the skin, fine holes are formed in the skin by a puncture tool beforehand, and the body fluid collection body is brought into close contact with the region where the holes are formed. When the predetermined time has elapsed, the body fluid collection sheet is removed from the skin and used for measurement.

In this case, some time may be required from the removal of the body fluid collection sheet until the measurement. For example, when the collection location of the body fluid and the measurement location are separated, it would be necessary to transport the removed body fluid collection sheet over a date and time. In such a case, means for adequately supporting the body fluid collection sheet while preventing contamination and drying of the body fluid collector is required.

Japanese Patent Application Publication No. 2014-143845 discloses a support kit for supporting a body fluid collection sheet. Here, as shown in FIGS. 17A and 17B, the body fluid collecting body holding sheet 600 affixed to the skin is removed from the skin and stuck on the application surface 700a of the supporting sheet 700. The user sticks the adhesive surface of the body fluid collecting body holding sheet 600 to the attachment surface 700a of the supporting sheet 700 so that the collecting bodies 601 and 602 of the body fluid collecting body holding sheet 600 enter the holes 701 and 702 of the supporting sheet 700.

SUMMARY OF THE INVENTION

In the support kit of Patent Application Publication 1, it is necessary for an operator to peel off the body fluid collection sheet directly from the skin with the fingers and paste it on the supporting sheet. This work needs to be done carefully and delicately so that the body fluid collector is not contaminated. For this reason, the work of installing the body fluid collection sheet on the support sheet is usually performed by medical staff such as a physician.

In view of this problem, the present invention provides a support body capable of easily supporting a body fluid collection sheet even by a non-physician, a body fluid collection set including the support body and the body fluid collection sheet, and a body fluid collection method.

A first aspect of the invention relates to a support body for supporting a body fluid collection sheet for collecting a body fluid both while maintaining contact with the skin and when separated from the skin after collection of the body fluid. The support body according to this is configured by a first sheet having an adhesive surface for adhering the body fluid collection sheet and a second sheet overlaid on the adhesive surface.

According to the support body of this aspect, after the collection of the body fluid is completed, the adhesive surface of the first sheet is attached to the body fluid collection sheet to separate the first sheet from the skin, whereby the body fluid collection sheet can be peeled off from the skin. Further, after the body fluid collection sheet is peeled off in this manner, the body fluid collection sheet can be supported between the first sheet and the second sheet by overlaying and adhering the second sheet to the adhesive surface of the first sheet.

According to the support body of this aspect, the worker does not directly touch the body fluid collection sheet, and the body liquid collection sheet can be supported by the first sheet and the second sheet in this way by a simple operation using the first sheet. Therefore, the body fluid collection sheet can easily be supported on the first sheet and the second sheet even by a non-physician.

Note that the adhesive surface of the first sheet may have an adhesive force capable of peeling the body fluid collecting sheet from the skin.

In the first aspect, the bodily fluid collection sheet may be a body fluid collecting body that adheres to the skin and collects bodily fluids. In this case, the second sheet has a hole through the second sheet disposed in a region where the body fluid collecting body is positioned when superimposed on the first sheet, and a peeling member which is peelably placed on a surface opposite to the surface of the second sheet overlaid on the first sheet and closes the hole from the opposite surface. In this way it is possible to expose the body fluid collecting body to the outside by a simple operation of peeling off the peeling member. Hence, the body fluid collector can be more conveniently used for measurement.

The second sheet also is preferably integrally provided with the first sheet so as to foldably overlap with the adhesive surface. In this way, after the adhesive surface of the first sheet is adhered to the body fluid collection sheet, the body fluid collection sheet is pulled away from the skin, and the second sheet then is folded onto the first sheet, so that the body fluid collection sheet is supported between the seat and the second seat.

In this case, the support body may further include a notch part provided at a boundary between the first sheet and the second sheet. In this way, the second sheet can be folded over easily on the adhesive surface of the first sheet since the second sheet is readily folded at a predetermined position.

In the support body according to the first aspect, the surface area of the adhesive surface of the first sheet may be set larger than the surface area of the body fluid collection sheet. In this way, the second sheet can be adhered appropriately to the adhesive surface of the first sheet in a state in which the body fluid collection sheet is adhered to the adhesive surface of the first sheet.

In the first aspect, the bodily fluid collection sheet may be a body fluid collecting body that adheres to the skin and collects bodily fluids. In this case, the first sheet may be formed as transparent or semitransparent and include a marker indicating a region where the body fluid collector is to be positioned. In this way, the operator confirms the position of the body fluid collecting body on the skin through the first sheet, and adheres the first sheet on the body fluid collection sheet so that the body fluid collecting body is positioned in the predetermined region indicated by the marker.

The support body according to the first aspect may further include a third sheet integrally formed on the second sheet and which is foldable with the second sheet. According to this configuration, the second sheet can be cleanly protected by folding the third sheet on the second sheet in a state before use.

In this case, the support body may further include a notch part provided at a boundary between the second sheet and the third sheet. In this way, the third sheet can be folded over easily from the second sheet since the third sheet is readily folded at a predetermined position.

The third sheet also may be configured to have an adhesive surface for adhering to the second sheet. In this case, the adhered surface of the second sheet can be protected more reliably with the third sheet since the third sheet does not undesirably separate from the second sheet.

Note that the adhesive surface of the third sheet preferably is a weakly sticky adhesive surface that can prevent deviation from the second sheet and allows the third sheet to be easily peeled from the second sheet.

For example, the adhesive strength of the adhesive surface of the third sheet preferably is weaker than the adhesive strength of the adhesive surface of the first sheet. In this way, the third sheet can be easily separated from the second sheet.

In unused condition, the support body may be in a state in which the third sheet is folded over the second sheet and the first sheet is folded over the third sheet. In this way, since the first sheet to be used first is positioned on the outermost side of the support body, it is possible to peel off from the first sheet and smoothly continue to support the body fluid collection sheet.

In this case, the third sheet preferably has a non-adhesive surface on the opposite side to the adhesive surface of the third sheet. In this way, the first sheet can be easily peeled from the back surface of the third sheet folded over the adhered surface of the second sheet.

In a state in which the adhesive surface of the first sheet is overlaid and adhered to the surface of the third sheet on the opposite side to the adhesive surface, the first sheet also may be configured to provide a flange part protruding from the side edge of the contour composed of the third sheet and the second sheet. In this way, the operator can peel off the first sheet from the third sheet more easily by gripping the flange part.

The third sheet also may be configured to provide a flange part protruding from a side edge of the second sheet in a state where the third sheet is overlaid and adhered to the second sheet. In this way, the operator can peel off the third sheet from the second sheet more easily by gripping the flange part.

A second aspect of the invention relates to a body fluid collection set. A bodily fluid collection set according to this aspect of the invention provides a body fluid collection sheet for collecting a body fluid in a state in which contact with the skin is maintained, a first sheet having an adhesive surface for adhering the body fluid collection sheet, and a second sheet adhered to the first sheet.

According to the body fluid collection set of this aspect, after the collection of the body fluid is completed, the adhesive surface of the first sheet is attached to the body fluid collection sheet and the first sheet is separated from the skin, whereby the body fluid collection sheet can be peeled off from the skin. Further, after the body fluid collection sheet is peeled off in this manner, the body fluid collection sheet can be supported between the first sheet and the second sheet by overlaying and adhering the second sheet to the adhesive surface of the first sheet.

According to the body fluid collection set of this aspect, the worker does not directly touch the body fluid collection sheet, and the body fluid collection sheet can be supported by the first sheet and the second sheet by a simple operation using the first sheet. Therefore, the body fluid collection sheet can easily be supported on the first sheet and the second sheet even by a non-physician.

Note that the adhesive surface of the first sheet may have an adhesive force capable of peeling the body fluid collecting sheet from the skin.

In the body fluid collection set according to this aspect, the body fluid collection sheet may include a body fluid collection body for collecting a body fluid, and an adhesive sheet for bringing the body fluid collection body into contact with the skin.

In this case, the body fluid collection sheet may include a first body fluid collecting body for collecting interstitial fluid and a second body fluid collecting body for collecting perspiration. In this way both tissue fluid and perspiration can be collected from the same patient's skin.

In the body fluid collection set according to this aspect, the adhesive strength of the adhesive surface of the first sheet can be adjusted to be stronger than the adhesive strength of the adhesive sheet. In this way, the body fluid collection sheet can be peeled from the skin more reliably using the first sheet.

The body fluid collection set also may include a puncture tool for forming fine holes in the skin to collect bodily fluids by the body fluid collection sheet. As a result, the worker can form minute holes in the skin using the puncture tool and collect the interstitial fluid from the skin.

A third aspect of the invention relates to a body fluid collection method in which body fluid is collected using a body fluid collecting body that collects body fluid while maintaining a state of contact with the skin, and subsequently the body fluid collection sheet is supported by a support body when the body fluid collection sheet is peeled from the skin. Here, the support body includes a first sheet having an adhesive surface and a second sheet adhered to the adhesive surface. The body fluid collection method according to this aspect includes a step of adhering the adhesive surface of the first sheet to the body fluid collection sheet, and a step of folding the second sheet on the adhesive surface of the first sheet to support the body fluid collection sheet between the first sheet and the second sheet.

According to the body fluid collection method of this aspect, the operator can support the body fluid collection sheet that has collected the body fluid from the skin on the first sheet and the second sheet by a simple operation, similarly to the first embodiment. Therefore, the body fluid collection sheet can be supported easily even by a non-physician.

In the body fluid collection method according to this aspect, the second sheet may be provided integrally with the first sheet so as to be foldable with the adhesive surface. In this case, an operation is performed to fold the second sheet on the adhesive surface of the first sheet, and adhere the second sheet to the adhesive surface in the step of supporting the body fluid collecting sheet. In this way, after the adhesive surface of the first sheet is adhered to the body fluid collection sheet, the body fluid collection sheet is pulled away from the skin, and the second sheet then is folded onto the first sheet, so that the body fluid collection sheet is supported between the seat and the second seat.

In the body fluid collection method according to this aspect, a third sheet is preferably peelably provided on the adhered surface of the second sheet to which the pressure-sensitive adhesive surface of the first sheet is adhered. In this way, it is possible to hygienically protect the adhered surface of the second sheet with which the body fluid collection sheet may come into contact via the third sheet, so that contamination of the body fluid collection sheet can be prevented.

In this case, it is preferable that the third sheet is peeled from the second sheet before the step of supporting the body fluid collection sheet. The body fluid collection sheet is preferably supported between the first sheet and the second sheet after the second sheet is overlaid on the adhesive surface of the first sheet in a state in which the third sheet has been peeled from the second sheet in the step of supporting the body fluid collection sheet. In this way, the operator can easily and smoothly support the body fluid collection sheet without contamination, since the adhered surface of the second sheet is protected by the third sheet until just before the second sheet is overlaid on the first sheet.

The third sheet also is integrally provided on the second sheet so as to be foldable on the adhered surface of the second sheet on which the adhesive surface of the first sheet is overlaid, and the body fluid collection method includes a step of folding the third sheet on the surface on the opposite side to the adhesive surface of the first sheet after overlaying the second sheet on the adhesive surface of the first sheet in the step of supporting the first sheet. In this way, the second sheet can be prevented from peeling away from the first sheet after supporting the body fluid collection sheet, so that the body fluid support sheet can be more reliably and stably supported by the support body.

According to the invention, the body fluid collection sheet can be easily supported on the support body by a non-physician.

BRIEF DESCRIPTION OF THE DRAWINGS

FIG. 2A is a view of the support body in an unfolded state as viewed from the upper side, and FIG. 2B is a view of the support body in the unfolded state as seen from below;

FIG. 8 is a flow chart showing the body fluid collection method according to the first embodiment;

DETAILED DESCRIPTION OF THE PREFERRED EMBODIMENTS

First Embodiment

The support body of the first embodiment supports a body fluid collection sheet for percutaneously collecting interstitial fluid and perspiration. Two body fluid collection bodies in gel form are installed in the body fluid collection sheet for transdermal collection of interstitial fluid and perspiration. The collected interstitial fluid is used for measurement of blood glucose level. Perspiration is used to correct measured values. The number of body fluid collecting bodies provided in the body fluid collecting sheet is not limited to two, and may be one, three or more.

Figure 1A:
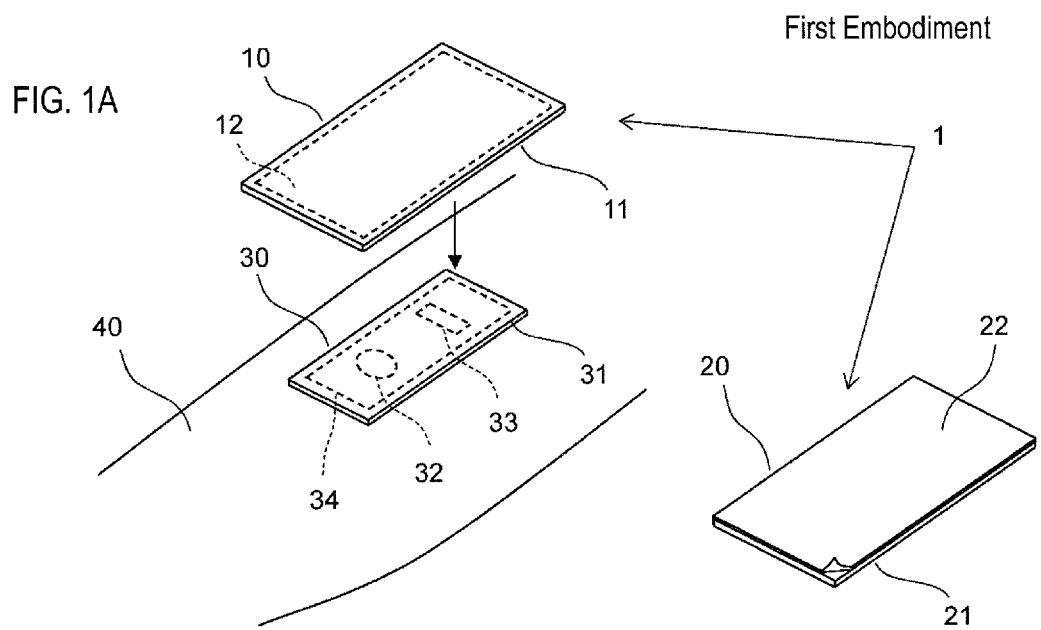
FIGS. 1A through 1C are conceptual diagrams illustrating a basic configuration and a usage method of a body fluid collection set according to a first embodiment.
Figure 1B:
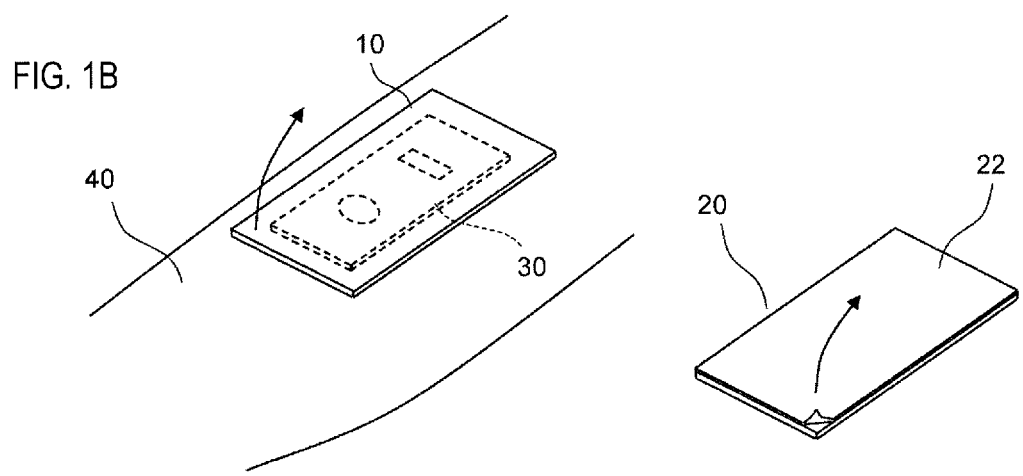
Figure 1C:
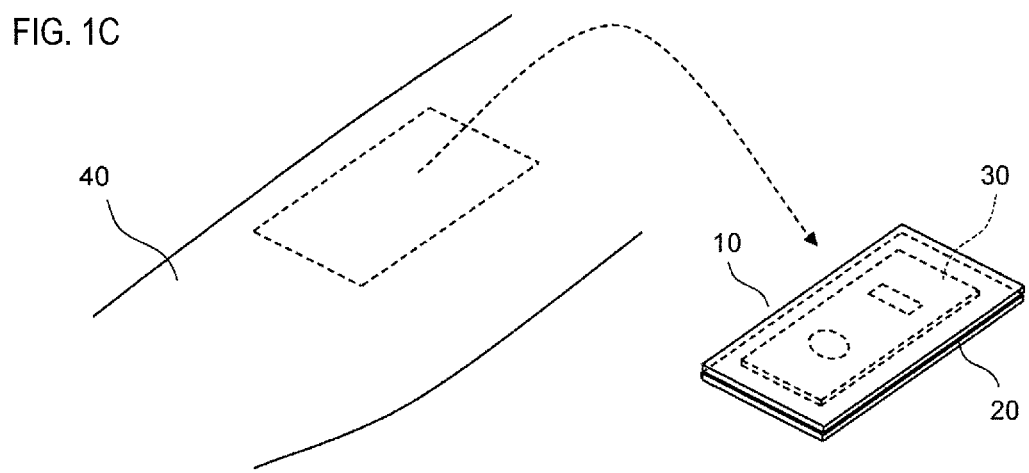

As shown in FIGS. 1A through 1C, the support body 1 is configured by a first sheet 10 and a second sheet 20. In plan view, the first sheet 10 and the second sheet 20 have rectangular shapes of the same size. The shape of the first sheet 10 and the second sheet 20 is not limited to a rectangle, and may be other shapes such as a circle, an ellipse and the like. The sizes of the first sheet 10 and the second sheet 20 also are not necessarily the same. The second sheet 20 is sufficient insofar as it can be adhered to cover both the first body fluid collection body 32 and the second body fluid collection body 33 on the body fluid collection sheet 30 adhered to the first sheet 10.

The first sheet 10 is configured such that an adhesive surface 12 is formed on the bottom surface of a thin substrate 11. The substrate 11 is made of, for example, a flexible and transparent resin material such as polyethylene terephthalate. The substrate 11 and the adhesive surface 12 are preferably made of a transparent or translucent material so that the body fluid collection sheet 30 affixed to the skin 40 can be seen from above through the first sheet 10. In this way, the first sheet 10 can be attached to the body fluid collection sheet 30 while placing the first body fluid collection body 32 and the second body fluid collection body 33 at predetermined positions on the adhesive surface 12 of the first sheet 10.

The adhesive surface 12 of the first sheet 10 may have an adhesive force capable of peeling the body fluid collection sheet 30 from the skin 40 by adhering the adhesive surface 12 to the body fluid collection sheet 30 and separating it from the skin 40. For example, the adhesive strength of the adhesive surface 12 is set to be stronger than the adhesive strength of the adhesive sheet 31 configuring the body fluid collection sheet 30. In this way, the adhesive force when the adhesive face 12 is adhered to the upper surface of the adhesive sheet 31 is greater than the adhesive force between the adhesive surface 34 formed on the bottom face of the adhesive sheet 31 and the skin 40. As a result, the body fluid collection sheet 30 can be peeled off smoothly from the skin 40 by separating the first sheet 10 from the skin 40 in a state where the adhesive surface 12 of the first sheet 10 is adhered to the upper surface of the adhesive sheet 31.

The second sheet 20 has a configuration in which a protective film 22 is adhered on the top surface of a thin substrate 21. The substrate 21 is formed of, for example, the same material as the substrate 11 of the first sheet 10. The protective film 22 is for protecting the top surface of the substrate 21 from contamination. The bottom surface of the protective film 22 is a weakly viscous adhesive surface so that the protective film 22 can be easily peeled off from the substrate 21. A release treatment such as silicon coating also may be applied to the top surface of the substrate 21 so that the protective film 22 is easily peeled off.

The body fluid collection sheet 30 includes an adhesive sheet 31, a first body fluid collection body 32, and a second body fluid collection body 33. The bottom surface of the adhesive sheet 31 is an adhesive surface 34. The adhesive sheet 31 has a rectangular outline which is several steps smaller than the first sheet 10 in plan view. The first body fluid collection body 32 and the second body fluid collection body 33 are installed on the bottom surface of the adhesive surface 34. The first body fluid collection body 32 is used for collecting interstitial fluid and the second body fluid collection body 33 is used for perspiration collection. The adhesive sheet 31 is made of, for example, a flexible and transparent resin material such as polyethylene terephthalate. The adhesive sheet 31 and the adhesive surface 34 are preferably transparent or translucent so that the first body fluid collection body 32 and the second body fluid collection body 33 can be visually recognized from above through the adhesive sheet 31 in a state where the adhesive surface 34 is adhered to the skin 40.

When collecting body fluids, an operator first forms numerous fine pores in the skin with a puncturing tool (not shown). Next, as shown in FIG. 1A, the operator sticks the body fluid collection sheet 30 to the skin 40 so that the first body fluid collecting body 32 contacts the region where the hole is formed. Subsequently, after the time required for body fluid collection has elapsed, the operator adheres the adhesive surface 12 of the first sheet 10 to the top surface of the adhesive sheet 31 as shown in FIG. 1B. Then, the operator separates the first sheet 10 from the skin 40 and peels the body fluid collection sheet 30 together with the first sheet 10 from the skin 40.

Next, the operator peels off the protective film 22 from the second sheet 20. The operation of peeling off the protective film 22 from the second sheet 20 may be performed before adhering the first sheet 10 to the body fluid collection sheet 30 or before separating the first sheet 10 from the skin 40 after adhering the first sheet 10 to the body fluid collection sheet 30. Then, as shown in FIG. 1C, the operator superposes the first sheet 10 on which the body fluid collection sheet 30 is adhered on the top surface of the second sheet 20. In this way, the adhesive surface 12 of the first sheet 10 is adhered to the top surface of the second sheet 20, and the body fluid collection sheet 30 is supported sandwiched between the first sheet 10 and the second sheet 20.

In the state of FIG. 1C, the adhesive surface 12 adheres to the top surface of the second sheet 20 in all regions around the body fluid collection sheet 30. Therefore, the body fluid collection sheet 30 is sealed between the first sheet 10 and the second sheet 20.

According to the steps of FIGS. 1A through 1C, the operator can peel off the body fluid collection sheet 30 from the skin 40 by an operation on the larger first sheet 10 without direct contact with the smaller body fluid collection sheet 30. Therefore, the first body fluid collection body 32 and the second body fluid collection body 33 are not contaminated in the operation of peeling the body fluid collection sheet 30 from the skin 40. Therefore, the body fluid collection sheet 30 easily can be supported on the support body 1 without contamination even by a non-physician, and, for example, the operation of collecting body fluids and the operation of supporting the body fluid collection sheet 30 using the support body 1 can be performed even at home.

Note that the first sheet 10 and the second sheet 20 are not necessarily separate from each other. The first sheet 10 and the second sheet 20 may be integrated so that the first sheet 10 can be folded over the second sheet 20.

SPECIFIC STRUCTURAL EXAMPLES

A specific configuration example of the support body 100, a method of collecting a body fluid using the body fluid collection sheet 200, and a method of supporting the body fluid collection sheet 200 with respect to the support body 100 will be described with reference to FIGS. 2A through 13B. X, Y, and Z axes orthogonal to each other are added in each drawing. In the state in which the support body 100 is unfolded, the surface on the Z-axis positive side is the top surface and the surface on the negative Z-axis side is the bottom surface.

Figure 2A:
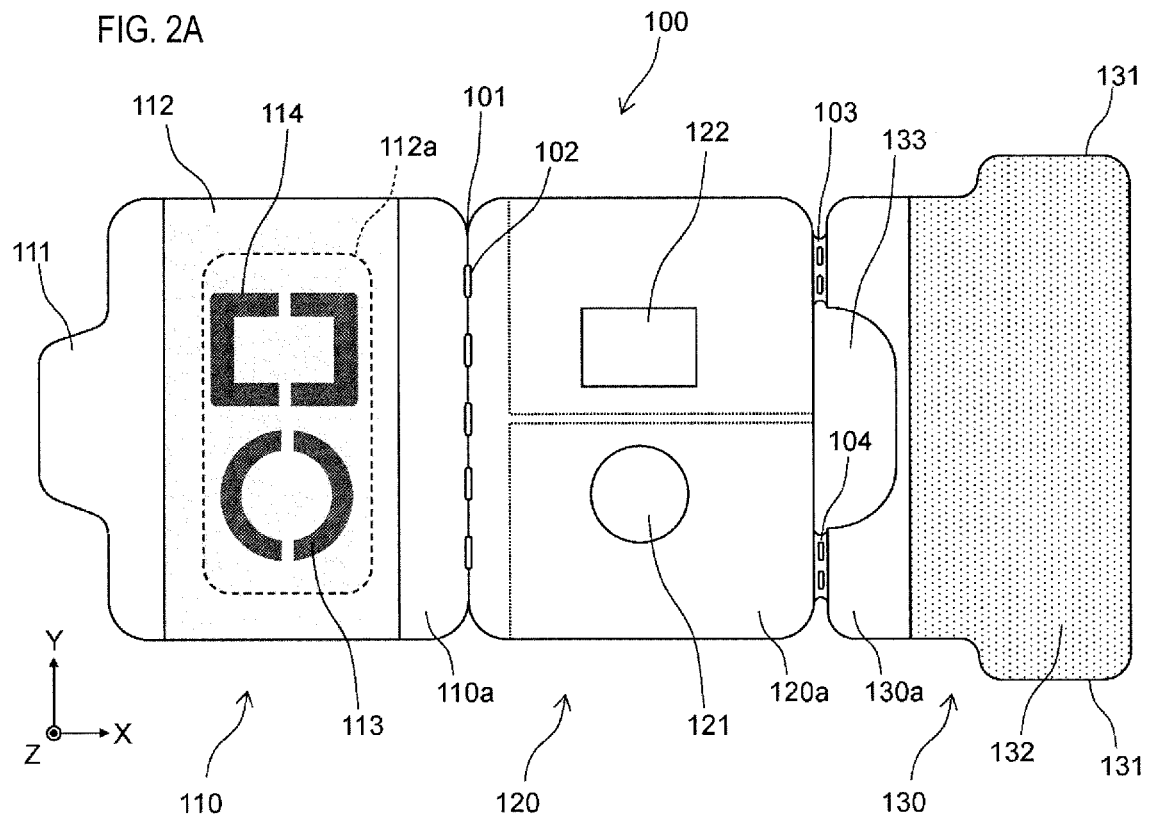
FIGS. 2A and 2B are plan views showing concrete configuration examples, respectively, of a support body according to the first embodiment.
Figure 2B:
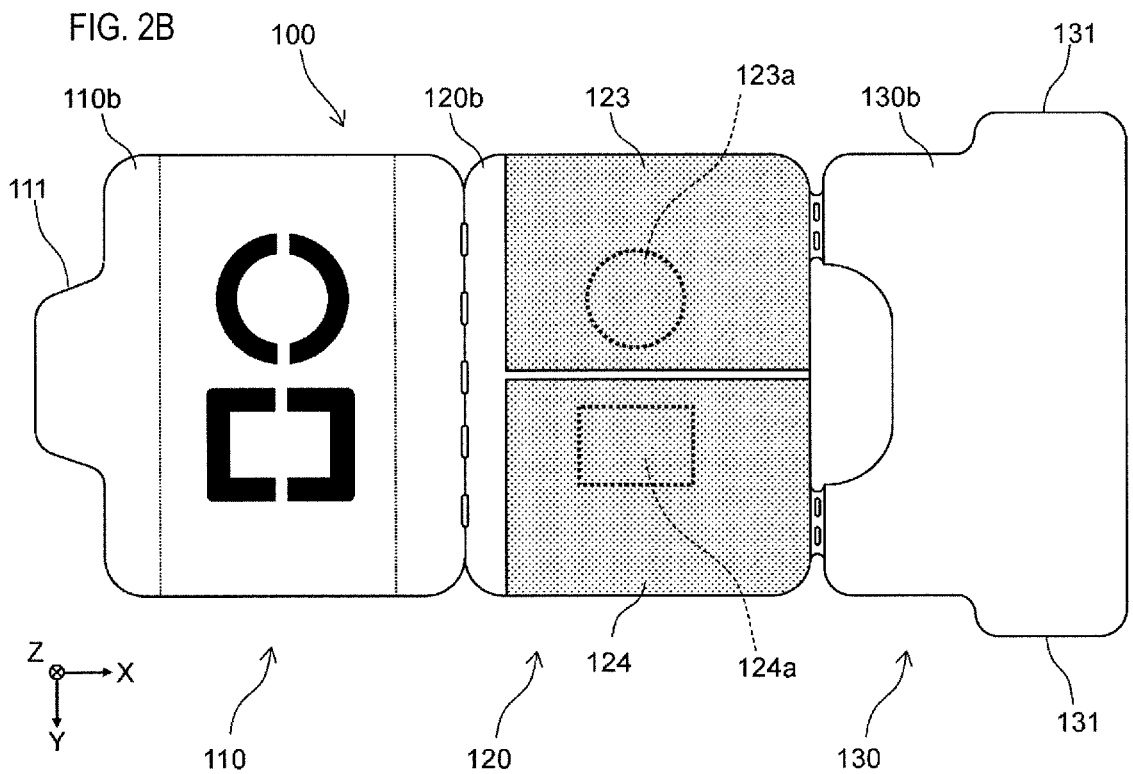
Figure 6A:
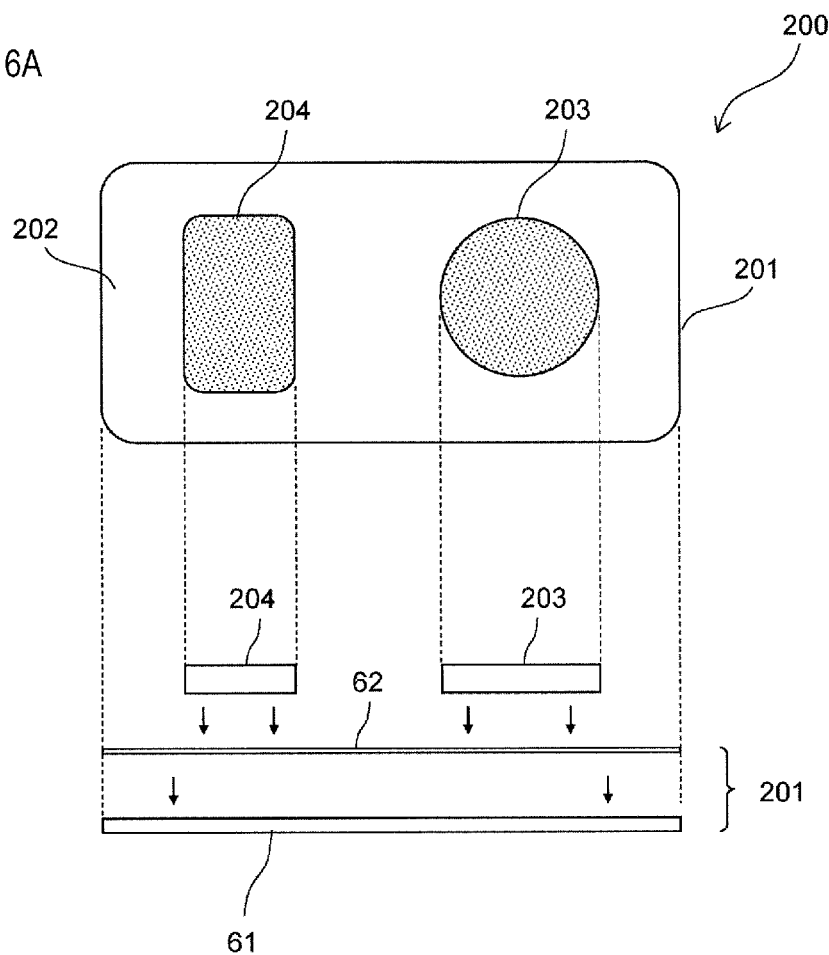
FIG. 6A is a plan view and a side view schematically showing a configuration of a body fluid collection sheet according to the first embodiment.
Figure 6B:
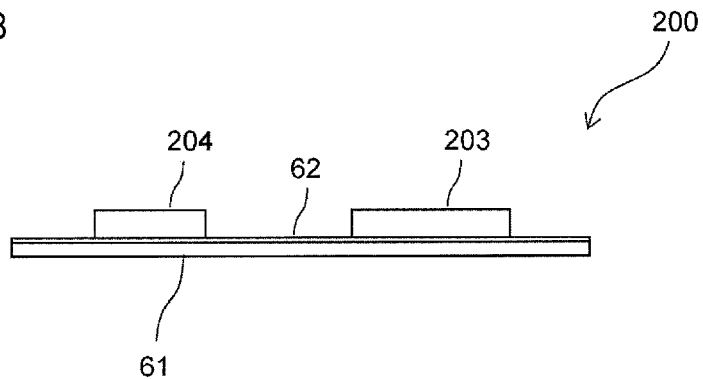
FIG. 6B is a plan view schematically showing the layer structure of the body fluid collection sheet according to the first embodiment.

In this configuration example, a body fluid collection set is configured by the support body 100 shown in FIGS. 2A and 2B, and the body fluid collection sheet 200 shown in FIGS. 6A and 6B. The body fluid collection set also may include the support body 100 and the body fluid collection sheet 200, as well as the puncture tool 300 shown in FIG. 7A.

As shown in FIGS. 2A and 2B, the support body 100 includes a first sheet 110, a second sheet 120, and a third sheet 130. The first sheet 110 and the second sheet 120 respectively correspond to the first sheet 10 and the second sheet 20 shown in FIGS. 1A through 1C. The third sheet 130 corresponds to the protective film 22 of FIGS. 1A through 1C, and is provided to protect from contamination the top surface 120a of the second sheet 120, that is, the adhered surface to which the adhesive surface 112 of the first sheet 110 is adhered.

The first sheet 110 is integrated with the second sheet 120 by a connecting portion 101 that extends in the Y-axis direction. A notch 102 penetrating the connecting portion 101 is provided at regular intervals along the connecting portion 101. In this way, the first sheet 110 is integrated with the second sheet 120 so as to be easily foldable on the second sheet 120.

The third sheet 130 is integrated with the second sheet 120 by two connecting portions 103 that extend in the Y-axis direction. A notch 104 penetrating the connecting portions 103 is provided at regular intervals along the connecting portions 103. In this way, the third sheet 130 is integrated with the second sheet 120 so as to be easily foldable on the second sheet 120.

A flange part 111 that protrudes toward the X-axis negative side is formed at the center of the X-axis negative side end portion of the first sheet 110. As will be described later, the flange part 111 is grasped by an operator when the first sheet 110 is peeled from the lower surface 130b of the third sheet 130. The position of the flange part 111 is not limited to the positions in FIGS. 2A and 2B, and may be, for example, the end portion on the Y-axis positive side of the first sheet 110. Except for the flange part 111, the first sheet 110 has a rectangular rounded corner outline. The first sheet 110 has a contour that is symmetrical in the Y-axis direction.

An adhesive surface 112 having a predetermined width is formed on the top surface 110a of the first sheet 110. The formation area of the adhesive surface 112 is wider than the adhesion area 112a of the body fluid collection sheet 200 (see FIG. 6A) by several steps. The area of the adhesive surface 112 may be of any other size insofar as the second sheet 120 can stick to the adhesive surface 12 in a state in which the body fluid collection sheet 200 is adhered to the adhesive surface 12. The size of the adhesive surface 112 is preferably sufficiently large so that the adhesive surface 112 adheres to the top surface of the second sheet 20 over the entire periphery of the body fluid collection sheet 200 and seals the body fluid collection sheet 200 when the first sheet 110 is folded over the top surface of the second sheet 120. For example, the adhesive surface 112 may be formed in the region of the top surface 110a excluding the flange part 111.

The adhesive strength of the adhesive surface 112 is an adhesive strength capable of peeling the body fluid collection sheet 200 from the skin 400 similar to the adhesive surface 12 of FIGS. 1A through 1C. The adhesive strength of the adhesive surface 112 is set to be stronger than the adhesive force of the adhesive sheet 201 configuring the body fluid collection sheet 2000.

A marker 113 composed of a circular arc frame and a marker 114 formed of a rectangular frame are further arranged on the top surface 110a of the first sheet 110. The marker 113 indicates the arrangement position of the first body fluid collection body 203 of the body fluid collection sheet 200 and the marker 114 indicates the arrangement position of the second body fluid collection body 204 of the body fluid collection sheet 200. The regions circumscribed by the markers 113 and 114 are the arrangement positions of the first body fluid collection body 203 and the second body fluid collection body 204, respectively (see FIG. 6A). The area circumscribed by the markers 113 and 114 is wider than the first body fluid collecting body 203 and the second body fluid collecting body 204. The bottom surface 110b of the first sheet 110 is a flat surface on which nothing is provided.

The first sheet 110 can visually confirm the Z-axis negative side from the Z-axis positive side except for the position of the marker 114. The area of the first sheet 110 excluding the position of the marker 114 is colorless and transparent. The area of the first sheet 110 excluding the position of the marker 114 may be colored or translucent. The color of the markers 113, 114 is, for example, black. If the markers 113 and 114 can be visually recognized, the markers 113 and 114 may be colors other than black and may be transparent or translucent.

The second sheet 120 has a rectangular rounded corner outline. The second sheet 120 has the same shape and size as the first sheet 110 except for the flange part 111. The first sheet 110 excluding the flange part 111 and the second sheet 120 completely overlap each other when the first sheet 110 is folded over the top surface 120a of the second sheet 120. The second sheet 120 is not necessarily the same shape and size as the first sheet 110. The seat 120 may have other shapes and sizes insofar as the body fluid collection sheet 200 is supported sandwiched between the first sheet 110 and the second sheet 120 by folding over and adhering the adhesive surface 112 of the first sheet 110 to the top surface 120a of the second sheet 120.

Holes 121 and 122 penetrating in the Z-axis direction are formed in the second sheet 120. The holes 121 and 122 are closed at the Z-axis negative side by the peeling members 123 and 124 adhered to the bottom surface 120b. When the first sheet 110 is folded over the upper surface 120a of the second sheet 120, the holes 121, 122 are formed at positions where the regions circumscribed by the markers 113, 114 are opposed to each other. The shape and the size of the holes 121 and 122 are substantially the same as the shape and size of the area circumscribed by the markers 113 and 114. The holes 121 and 122 also may be slightly larger than the region surrounded by the markers 113 and 114.

A release treatment such as silicone coating or the like is applied to the whole area of the top surface 120a of the second sheet 120. The region subjected to the releasing treatment is not necessarily the entire region of the top surface 120a of the second sheet 120, and may be limited to the area of contact of the adhesive surface 132 of the third sheet 130 when the third sheet 130 is folded over the top surface 120a of the second sheet 120.

Sheet-like peeling members 123 and 124 are peelably adhered on the bottom surface 120b of the second sheet 120. As described above, the peeling members 123 and 124 respectively near the holes 121 and 122 from the Z-axis negative side. Recesses 123a and 124a having the same shape and size as the holes 121 and 122 are formed at positions corresponding to the holes 121 and 122 on the Z-axis positive side surface of the peeling members 123 and 124. In this way, the areas of the holes 121 and 122 are a receiving parts that are deeper than the depth of the holes 121 and 122. As will be described later, the peeling members 123 and 124 are peeled from the bottom surface 120b of the second sheet 120 at the time of measurement.

Two flange parts 131 that protrude to the Y-axis positive side and Y-axis negative side are respectively formed on the third sheet 130 at a position at the corner of the Y-axis positive side and X-axis positive side, and at a position at the corner of the Y-axis negative side and X-axis positive side. As will be described later, the flange part 131 is grasped by an operator when the third sheet 130 is peeled from the bottom surface 120b of the second sheet 120. The position of the flange part 131 is not limited to the positions in FIGS. 2A and 2B, and may be, for example, the end portion on the X-axis positive side of the third sheet 130. Except for the flange part 131, the third sheet 130 has a rectangular rounded corner outline. The third sheet 130 has a contour that is symmetrical in the Y-axis direction.

The width in the Y-axis direction of the third sheet 130 is the same as the width in the Y-axis direction of the second sheet 120. The width in the X-axis direction of the third sheet 130 is slightly smaller than the width in the X-axis direction of the second sheet 120. The third sheet 130 may have other shapes and sizes insofar as the third sheet 130 can cover the area of the second sheet 120 that is in contact with the adhesion area 112a when the first sheet 110 is folded over the second sheet 120.

An adhesive surface 132 having a predetermined width is formed on the top surface 110a of the third sheet 130. The size of the adhesive surface 132 is not limited as long as the size can maintain the adhesion state of the third sheet 130 to the second sheet 120 in a state in which the third sheet 130 is folded over the top surface of the second sheet 120. For example, the adhesive surface 112 may be formed in the entire region of the top surface 110a of the third sheet 130.

The adhesive surface 132 is for temporarily fastening the third sheet 130 to the top surface 120a of the second sheet 120. The adhesive surface 132 of the third sheet 130 preferably is a weakly adhesive surface that can temporarily fasten the third sheet 130 to the second sheet 120, and can easily peel off the third sheet 130 from the second sheet 120. At least the adhesive strength of the adhesive surface 132 is weaker than the adhesive strength of the adhesive surface 112 of the first sheet 110. Instead of forming the adhesive surface 132 on the third sheet 130, a weakly adhesive surface for temporarily fastening the third sheet 130 may be formed on the top surface 120a of the second sheet 120. In either case, it is necessary to select a material which does not affect the measurement of the first body fluid collecting body 203 and the second body fluid collecting body 204 as a material constituting the adhesive surface since the top surface of the second sheet 120 contacts the surface on the first body fluid collection body 203 and the second body fluid collection body 204 side of the body fluid collection sheet 200, as will be described later. For example, an urethane-based material can be used as such a material.

A notch 133 is formed at the X-axis negative side end portion of the third sheet 130. As will be described later, the notch 133 is for passing through the flange part 111 of the first sheet 110 when the third sheet 130 is folded over the bottom surface 110b of the first sheet 110 after folding the first sheet 110 on the top surface 120a of the second sheet 120.

A release treatment such as silicone coating or the like is applied to the whole area of the bottom surface 130b of the third sheet 130. The region subjected to the releasing treatment is not necessarily the entire region of the bottom surface 130b of the third sheet 130, and may be limited to the area of contact of the adhesive surface 112 of the first sheet 110 when the first sheet 110 is folded over the bottom surface 130b of the third sheet 130.

A method of generating the support body 100 will be described next with reference to FIGS. 3A and 3B. In the lower part of FIG. 3A, the members configuring the region partitioned by the dashed line of the support body 100 shown in the upper part of FIG. 3A are shown separately in the Z-axis direction.

Figure 3A:
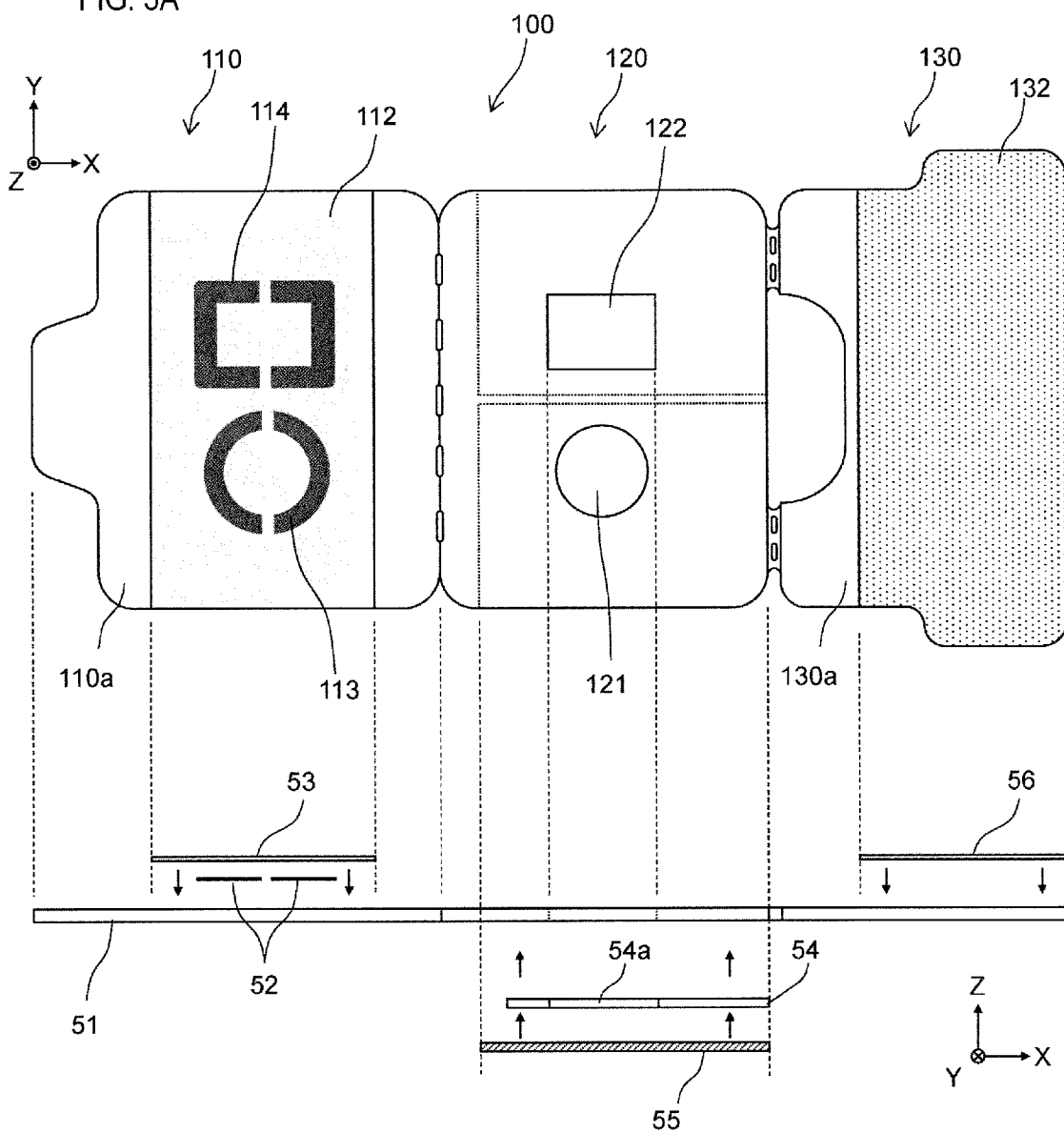
FIG. 3A is a plan view and a side view schematically showing a method for producing each sheet of the support body according to the first embodiment.

As shown in FIG. 3A, the support body 100 includes a substrate 51, members 52 and 55, and double-sided tape 53, 54, and 56. The substrate 51 is made of a transparent and flexible material such as polyethylene terephthalate. The double-faced tape 53, 54, and 56 are transparent. The double-sided tape 54 and 56 may be non-transparent. The double-sided tape 53 also may be semi-transparent.

In plan view, the substrate 51 has the same shape and size as the support body 100. Member 52 configures markers 113 and 114. The top surface of the double-sided tape 53 configures the adhesive surface 112. The double-sided tape 53 is adhered on the substrate 51 from the top side of the member 52. In this way, as shown in FIG. 3B, the member 52 is fixed to the substrate 51. Thus, the adhesive surface 112 and the markers 113 and 114 are arranged on the top surface 110a of the first sheet 110.

The member 55 and the double-sided tape 54 are integrated to form the peeling member 123 of FIG. 2B. The double-sided tape 54 is used to peelably adhere the member 55 to the bottom surface of the substrate 51. The width of the double-faced tape 54 in the Y-axis direction is the same as the member 55, and the width of the double-sided tape 54 in the X-axis direction is smaller than the member 55. The double-sided tape 54 has a hole 54a vertically penetrating at a position corresponding to the hole 121. The hole 54a constitutes the recess 123a of FIG. 2B. The bottom surface of the double-sided tape 54 is attached to the member 55 so that the end on the X-axis positive side is aligned. As shown in FIG. 3B, the top surface of the double-sided tape 54 also is attached to the bottom surface of the substrate 51. In this way, the peeling member 123 is disposed on the bottom surface 120b (see FIG. 2B) of the second sheet 120.

Figure 3B:
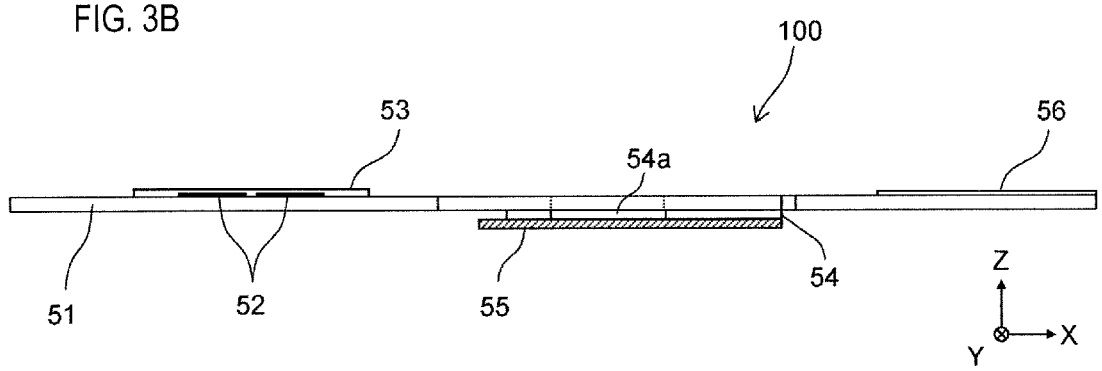
FIG. 3B is a plan view schematically showing the layer structure of the support body according to the first embodiment.

As shown in FIG. 3B, the end portion on the negative X-axis side of the member 55 protrudes from the double-sided tape 54. The operator can easily peel the member 55, that is, the peeling member 123 by catching a finger or a fingernail on this part. The adhesive strength between the double-faced tape 54 and the member 55 is greater than the adhesive strength between the double-faced tape 54 and the substrate 51. Therefore, when the member 55 is peeled off, the double-sided tape 54 remains on the top surface of the member 55 and is peeled off from the bottom surface of the substrate 51.

Note that, a double-sided tape and a member configuring the peeling member 124 are also mounted on the arrangement region of the peeling member 124 on the bottom surface of the substrate 51 in FIG. 2B. A hole having a shape corresponding to the hole 122 is formed in this double-sided tape. Other configurations of the double-faced tape and members configuring the peeling member 124 are the same as those of the double-sided tape 54 and the member 55.

The double-sided tape 56 has the same shape and size as the adhesive surface 132 of the third sheet 130. The top surface of the double-sided tape 56 configures the adhesive surface 132 of the third sheet 130. As shown in FIG. 3B, the top surface of the double-sided tape 56 is adhered to the bottom surface of the substrate 51. Thus, the adhesive surface 132 is arranged on the top surface 130a of the third sheet 130.

The pre-use folding mode of the support body 100 having the above configuration will be described next with reference to FIGS. 4A to 5B.

Figure 4A:
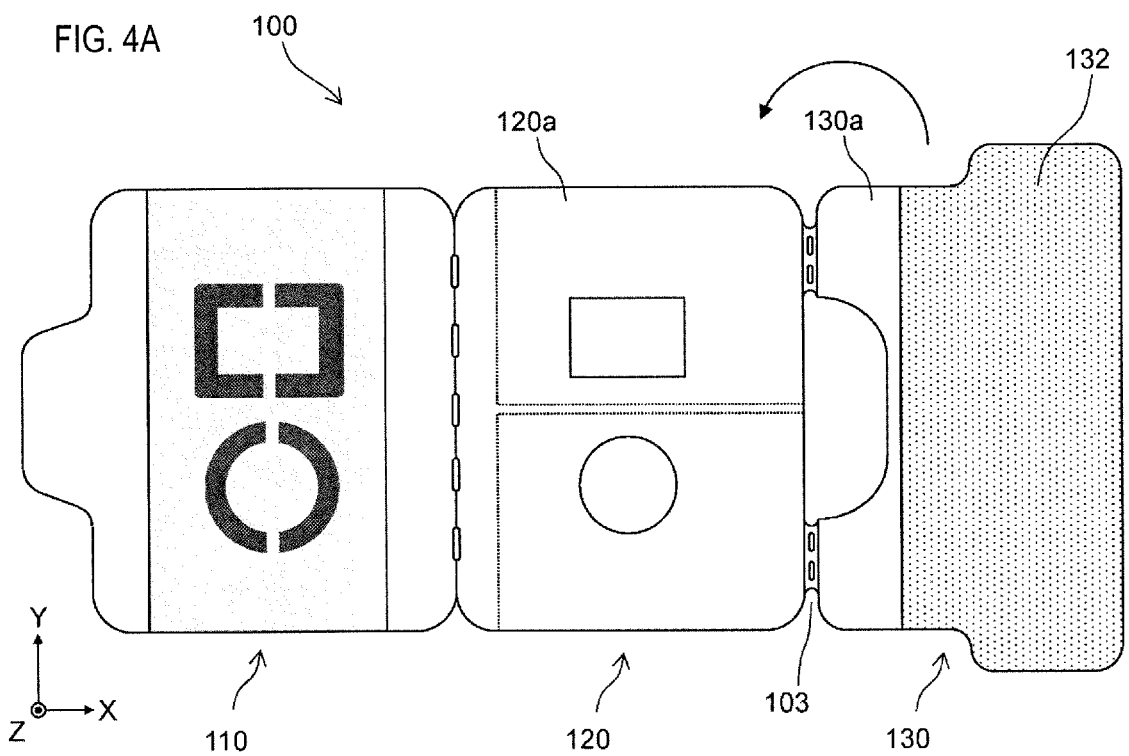
FIGS. 4A and 4B are plan views showing a folding process of each sheet when generating a support body before use according to the first embodiment.
Figure 4B:
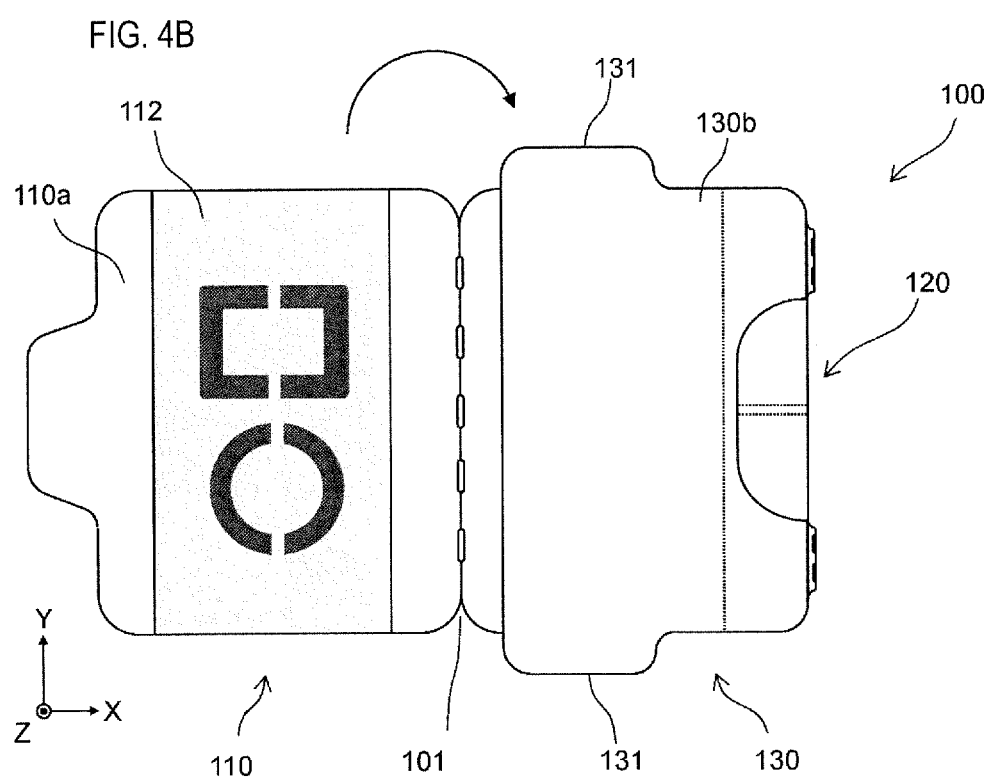

First, from the unfolded state shown in FIG. 4A, the support body 100 is folded over the third sheet 130 onto the top surface of the second sheet 120. At this time, the support body 100 is bent at the position of the connecting part 103. In this way, the adhesive surface 132 formed on the top surface 130a of the third sheet 130 adheres to the top surface 120a of the second sheet 120. Thus, the support body 100 is in the state of FIG. 4B. In this state, the flange part 131 protrudes from the side edge of the second sheet 120.

The third sheet 130 does not undesirably separate from the second sheet 120 since the third sheet 130 adheres to the second sheet 120 by the adhesive surface 132. The top surface 120a of the second sheet 120 therefore can be more reliably protected with the third sheet 130.

Figure 5A:
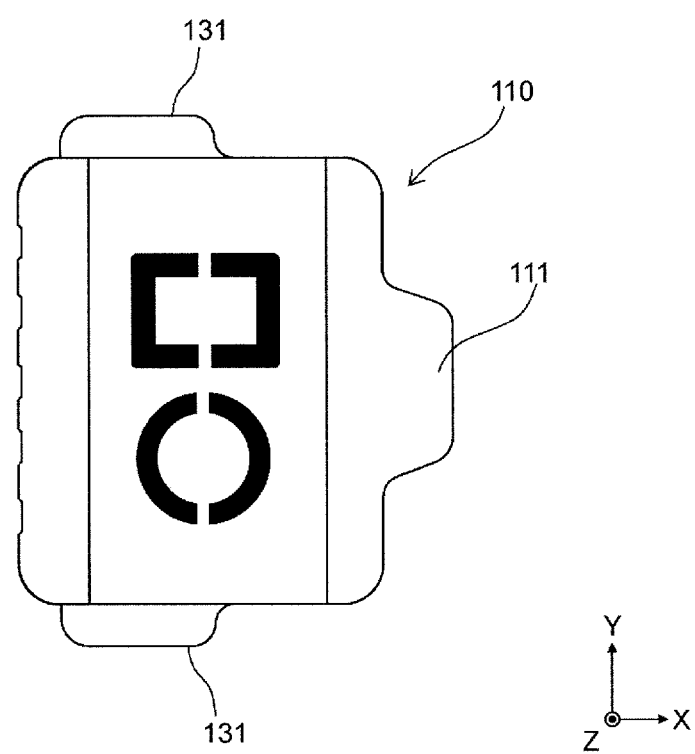
FIG. 5A is a plan view showing the final form of the support body before use according to the first embodiment.

Next, the first sheet 110 is folded over the bottom surface 130b of the third sheet 130 that is folded over the second sheet 120. At this time, the support body 100 is bent at the position of the connecting part 101. In this way, the adhesive surface 112 formed on the top surface 110a of the first sheet 110 adheres to the bottom surface 130b of the third sheet 130. Thus, the support body 100 is in the state shown in FIG. 5A. In this state, the flange part 111 protrudes from the side edge of the contour composed of the second sheet 120 and the third sheet 130. The state of FIG. 5A is the final form before use of the support body 100.

Figure 5B:
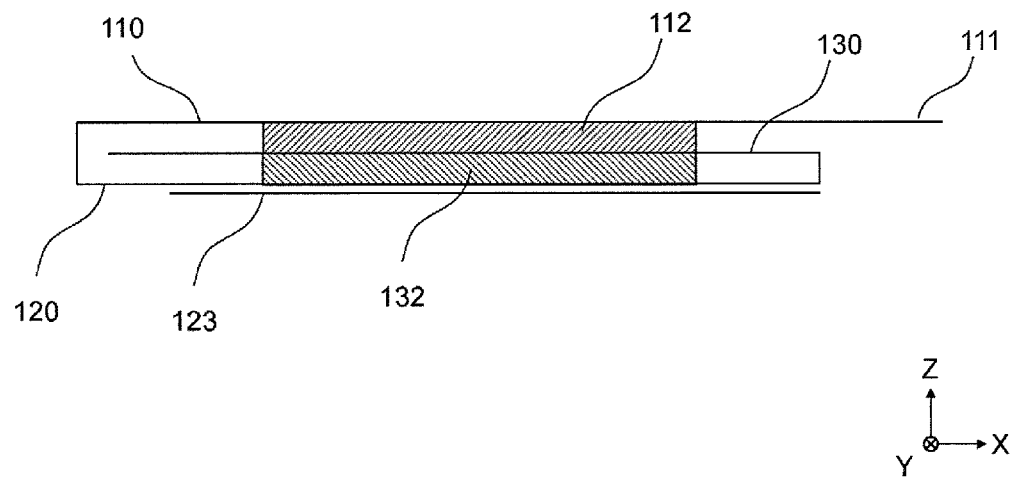
FIG. 5B is a diagram schematically showing the state of the final form of the support body before use according to the first embodiment when viewed from the side.

As schematically shown in FIG. 5B, the first sheet 110 is located on the outermost side in the final form before use. Therefore, in the final form before use, only the first sheet 110 can be unfolded among the first sheet 110, the second sheet 120, and the third sheet 130. The deployment order of the support body 100 is, first, the first sheet 110, and, second, the third sheet 130.

As will be described later, when supporting the body fluid collection sheet 200 on the support body 100, an operation is performed to first peel the body fluid collection sheet 200 from the skin 400 using the first sheet 110, and then an operation is performed to overlay the first sheet 110 on the top surface 120a of the second sheet 120. Therefore, by overlapping the sheets as shown in FIG. 5B the operator invariably unfolds from the first sheet 110 to be used for the first time, and the body fluid collection sheet 200 can be smoothly supported by the support body 100 without mistaking the order of peeling of the sheets.

Next, the configuration of the body fluid collection sheet 200 will be described with reference to FIGS. 6A and 6B. In the lower part of FIG. 6A, the members configuring the region partitioned by the dashed line of the body fluid collection sheet 200 shown in the upper part of FIG. 6A are shown separately in the Z-axis direction.

As shown in FIG. 6A, the body fluid collection sheet 200 includes an adhesive sheet 201, an adhesive surface 202 formed on one surface of the adhesive sheet 201, a first body fluid collection body 203 and a second body fluid collecting body 204. The adhesive sheet 201 has a rectangular rounded corner outline. The adhesive sheet 201 is a translucent flexible tape-like member. The adhesive surface 202 is formed in the entire region of one surface of the adhesive sheet 201. No pressure-sensitive adhesive surface is formed on the other surface of the adhesive sheet 201.

The first body fluid collecting body 203 is a gel which collects the tissue fluid percutaneously. The second body fluid collecting body 204 is a gel which collects the perspiration percutaneously. The first body fluid collecting body 203 and the second body fluid collecting body 204 are arranged linearly in the longitudinal direction of the adhesive sheet 201. Both the tissue fluid and perspiration can be acquired at the same time from the patient by installing the first body fluid collecting body 203 and the second body fluid collecting body 204 on the adhesive sheet 201.

As shown in the lower part of FIG. 6A, the adhesive sheet 201 of the body fluid collection sheet 200 is configured by a substrate 61 and a double-sided tape 62. The substrate 61 is a translucent tape-like member. The substrate 61 also may be configured of a transparent member. The double-sided tape 62 may be semi-transparent. The double-sided tape 62 also may be transparent. As shown in FIG. 6B, the double-sided tape 62 is adhered to the top surface of the substrate 61, and a first body fluid collection body 203 and a second body fluid collection body 204 are placed on the top surface of the double-sided tape 62. The top surface of the double-sided tape 62 configures the adhesive surface 202.

The adhesive surface 112 of the first sheet 110 shown in FIG. 3A is configured so that the adhesive strength when the adhesive surface 112 is adhered to the surface of the adhesive sheet 201 on the opposite side to the adhesive surface 202 is greater than the adhesive strength when the adhesive surface 202 of the adhesive sheet 201 is adhered to the skin 400. The adhesive strength of the adhesive surface 112 of the first sheet 110 is stronger than the adhesive strength of the adhesive surface 202 of the adhesive sheet 201.

Next, the configuration of the puncture tool 300 will be described with reference to FIG. 7A.

The puncture tool 300 includes a cylindrical main body 301, a button 302 protruding from the upper end of the main body 301, a cylindrical frame part 303 protruding from the lower end of the main body 301, a puncture needle 304 accommodated within the frame part 303, and a linking mechanism 305 for moving the puncture needle 304 downward in response to pressing of the button 302. The main body 301 has a size that allows grasping with one hand and pushing the button 302 with the thumb. The puncture needle 304 is configured by numerous non-invasive needle groups.

Figure 7A:
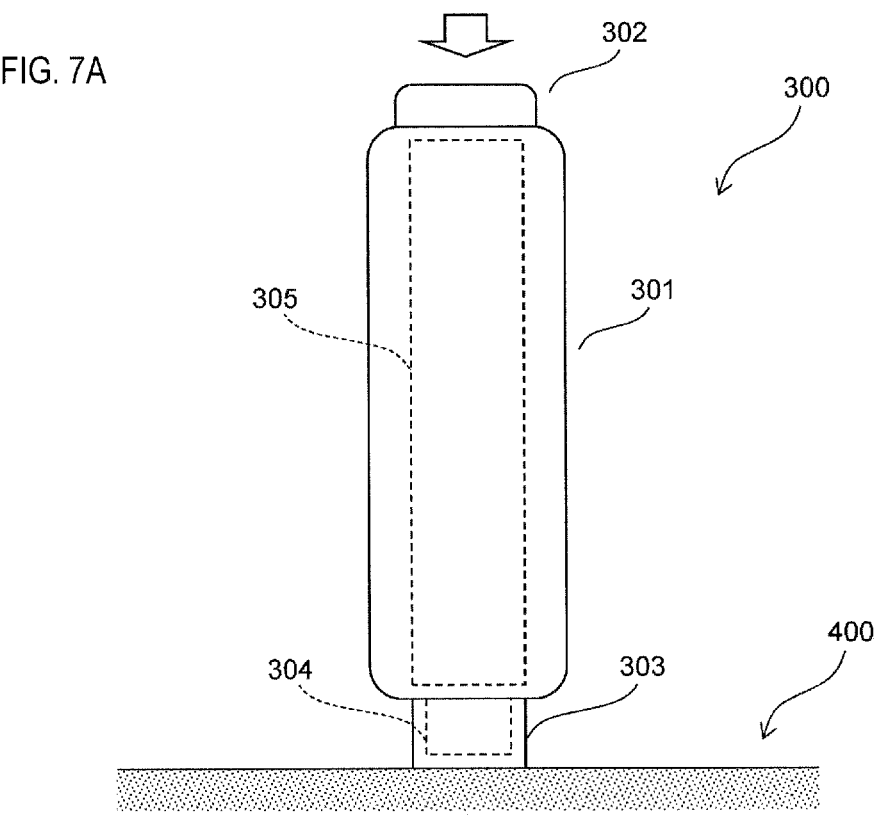
FIG. 7A is a side view schematically showing the configuration and usage of the puncture tool according to the first embodiment.
Figure 7B:
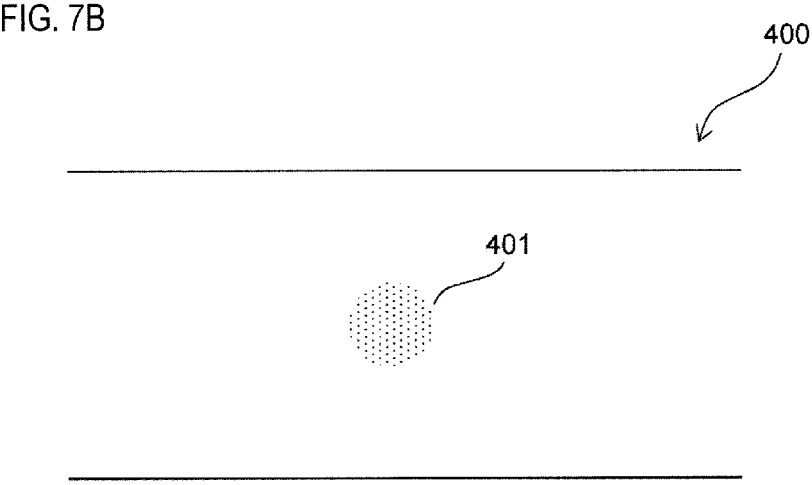
FIG. 7B is a diagram schematically showing a state in which holes are formed in the skin by the puncture tool according to the first embodiment.

As shown in FIG. 7A, when the button 302 is pushed with the lower end of the frame part 303 pressed against the skin 400, the puncture needle 304 moves downward and is pressed against the skin 400. In this way, as shown in FIG. 7B, a large number of fine holes 401 are formed in the skin 400. The first body fluid collection body 203 of the body fluid collection sheet 200 is applied to the region where the hole 401 is formed and the body fluid collection sheet 200 is adhered to the skin 400.

The work process at the time of body fluid collection will be described below with reference to FIG. 8.

In step S11, the operator forms fine holes 401 in the skin 400 of the patient's arm or the like using the puncture tool 300. The operator also may be the patient himself. In step S12, the operator presses the first body fluid collection body 203 of the body fluid collection sheet 200 against the region where the hole 401 was formed, and adheres the body fluid collection sheet 200 to the skin 400. At this time, the second body fluid collection body 204 is pressed against the surface of the skin 400 where the hole 401 has not been formed.

In step S13, the operator waits until the time required for body fluid collection has elapsed. Meanwhile, tissue fluid is percutaneously collected in the first body fluid collection body 203, and perspiration is collected in the second body fluid collection body 204. When the time required for body fluid collection has elapsed, in step S14, the operator performs the operation of peeling the first sheet 110 relative to the support body 100 before use.

Figure 9A:
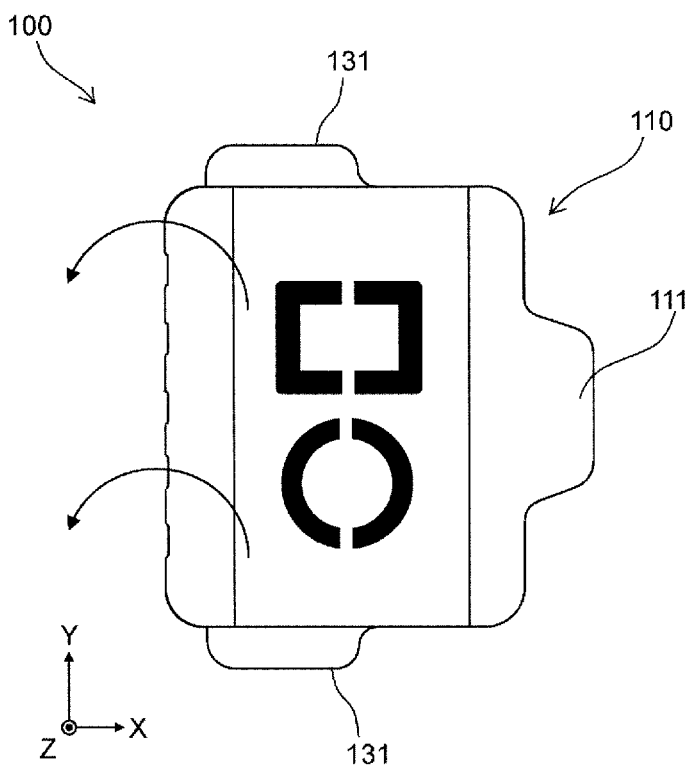
FIGS. 9A and 9B are plan views showing a process of unfolding a sheet when supporting a body fluid collection sheet on a support body according to the first embodiment.
Figure 9B:
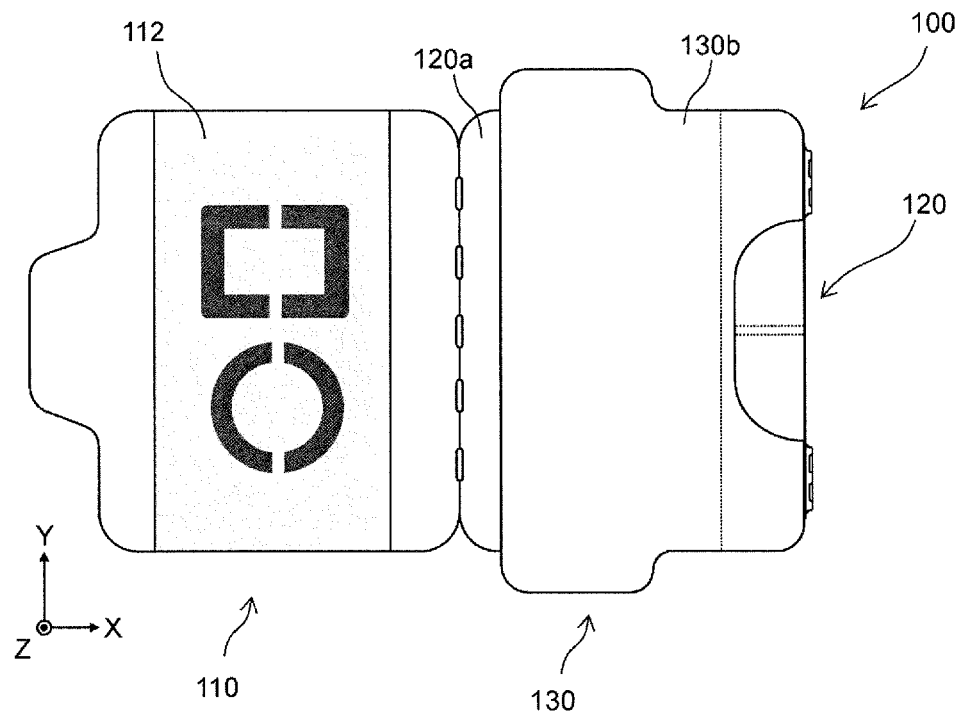

Specifically, as shown in FIG. 9A, the operator grips the flange part 111 with fingers to lift the first sheet 110. In this way, the support part 100 is unfolded as shown in FIG. 9B, and the adhesive surface 112 of the first sheet 110 is exposed. As described above, since the bottom surface 130b of the third sheet 130 is subjected to the releasing treatment, the operator can easily peel off the first sheet 110 from the state shown in FIG. 9A. The operator also can peel off the first sheet 110 from the third sheet 130 easily by gripping the flange part 111.

Returning to FIG. 8, then in step S15, the operator performs an operation of adhering the adhesive surface 112 of the first sheet 110 to the adhesive sheet 201 of the body fluid collection sheet 200 which is attached to the skin 400.

Figure 10A:
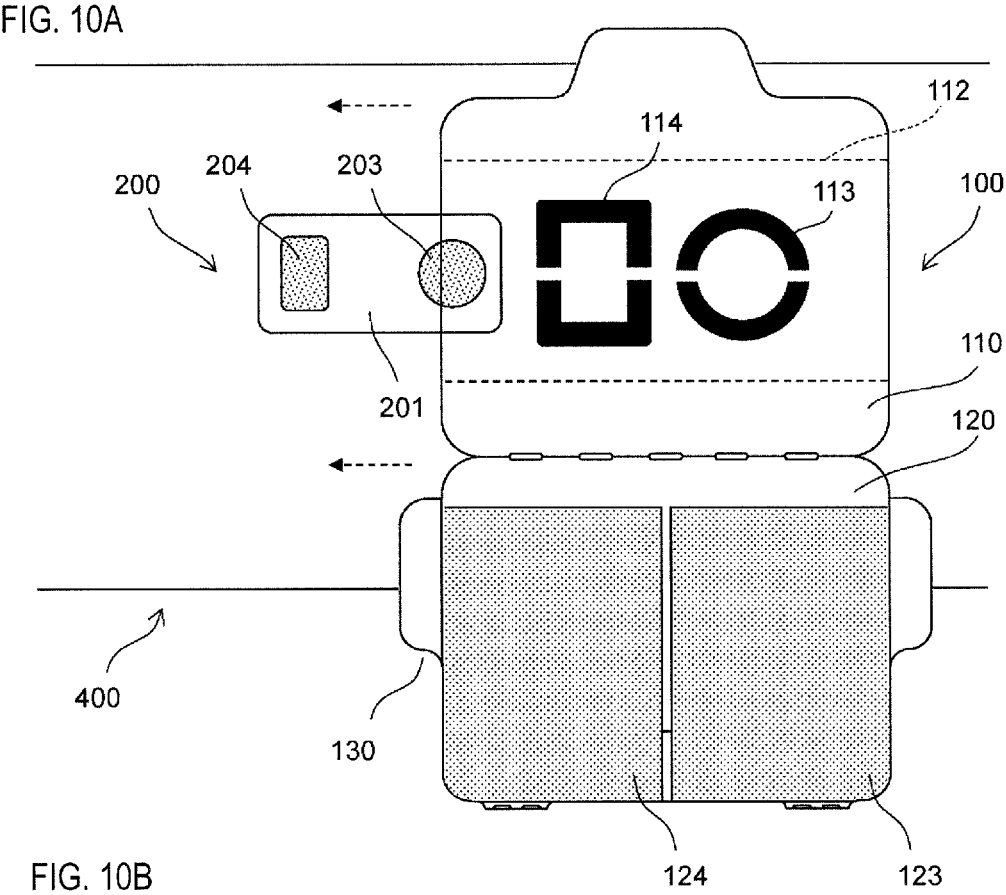
FIGS. 10A and 10B are plan views for describing a step of affixing the first sheet to a body fluid collection sheet according to the first embodiment.

Specifically, as shown in FIG. 10A, the operator grips the second sheet 120 and the third sheet 130 folded over each other with one hand, and the first sheet 110 is positioned above the body fluid collection sheet 200 which is adhered to the skin 400. In the state of FIG. 10A, the adhesive surface 112 of the first sheet 110 is on the skin 400 side. By slightly warping the parts of the second sheet 120 and the third sheet 130 that are folded over each other with the gripped fingers, the operator can prevent the first sheet 110 from drooping, and the first sheet 110 can be held in a substantially parallel state relative to the skin 400.

Figure 10B:
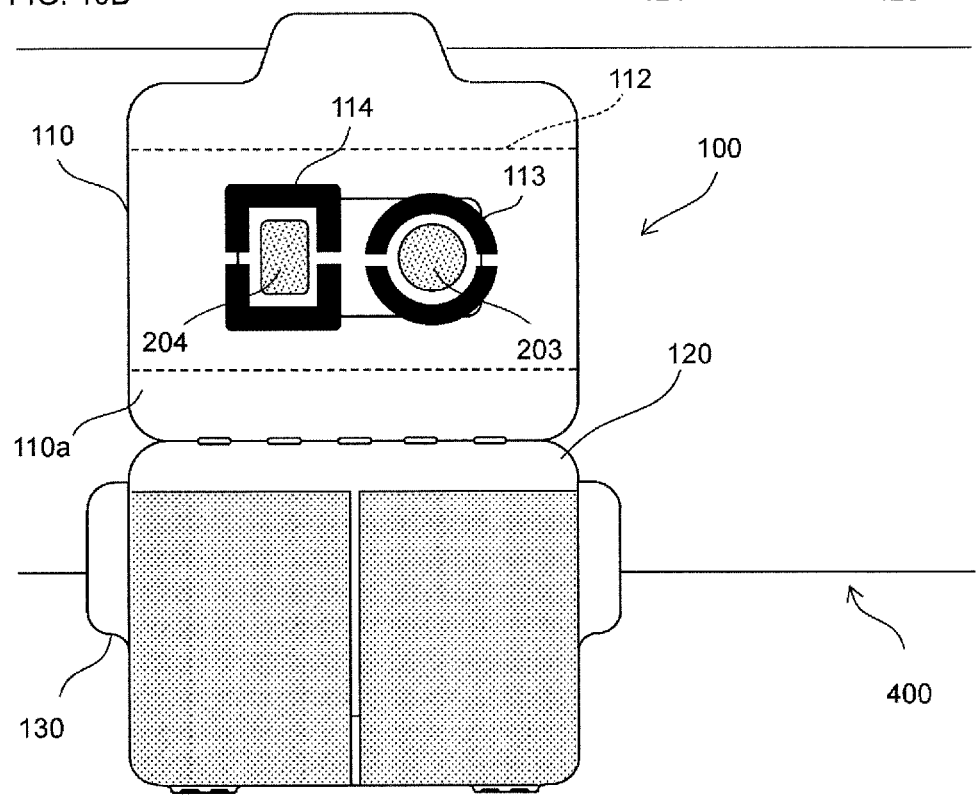

While observing the body fluid collection sheet 200 through the first sheet 110, the operator moves the support body 100 so as to align the regions circumscribed by the markers 113 and 114 with the first body fluid collection body 203 and the second body fluid collection body 204, respectively. In this state, the operator adheres the adhesive surface 112 of the first sheet 110 to the top surface of the adhesive sheet 201 of the body fluid collection sheet 200 as shown in FIG. 10B. The operator presses the bottom surface 110b of the first sheet 110 with a finger or the like, and securely adheres the adhesive surface 112 to the adhesive sheet 201.

While confirming the position of the body fluid collection sheet 200 on the skin 400 through the first sheet 110, the operator adheres the first sheet 110 on the body fluid collection sheet 200 so as to position the first body fluid collection body 203 and the second body fluid collection body 204 in the region indicated by the markers 113 and 114.

Thereafter, the operator lifts up the parts of the second sheet 120 and the third sheet 130 folded over each other, and separates the first sheet 110 from the skin 400. As described above, when separating the first sheet 110 from the skin 400, the first sheet 110 is pulled and the body fluid collection sheet 200 is peeled off from the skin 400 since the adhesive strength of the adhesive surface 112 is sufficiently greater than the adhesive strength between the skin 400 and the body fluid collection sheet 200. The operator can easily peel off the body fluid collection sheet 200 from the skin 400 without directly touching the body fluid collection sheet 200. In addition, contamination of the first body fluid collection body 203 and the second body fluid collection body 204 can be prevented since the body fluid collection sheet 200 is not touched when peeled from the skin 400.

Returning to FIG. 8, the operator peels off the third sheet 130 from the second sheet 120 in step S17.

Figure 11A:
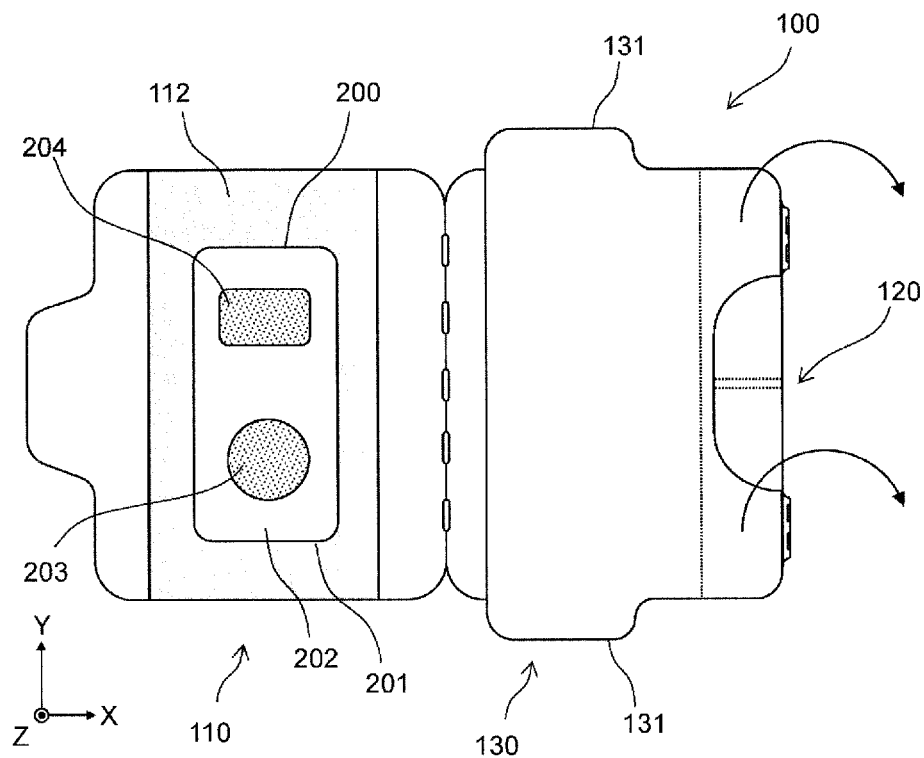
FIG. 11A is a plan view showing a process of developing a sheet when supporting a body fluid collection sheet on a support body according to the first embodiment.

Specifically, as shown in FIG. 11A, the operator grips the flange part 131 and lifts the third seat 130. The body fluid collection sheet 200 has already been peeled off from the skin 400 of an arm or the like at the timing of this operation. Therefore, the operator can also proceed with the work using both hands even when the patient himself is the operator.

For example, the operator grips the flange part 131 with the fingers of one hand while holding the vicinity of the boundary between the first sheet 110 and the second sheet 120 with the fingers of the other hand, and lifts the first sheet 110. As described above, the operator can easily peel off the third sheet 130 from the second sheet 120 since the adhesive surface 132 of the third sheet 130 is weakly adhesive. Since the top surface 120a of the second sheet 120 is subjected to the releasing treatment as described above, the operator can peel the third sheet 130 from the second sheet 120 more easily. The operator also can peel off the third sheet 130 from the second sheet 120 easily by gripping the flange part 131.

Figure 11B:
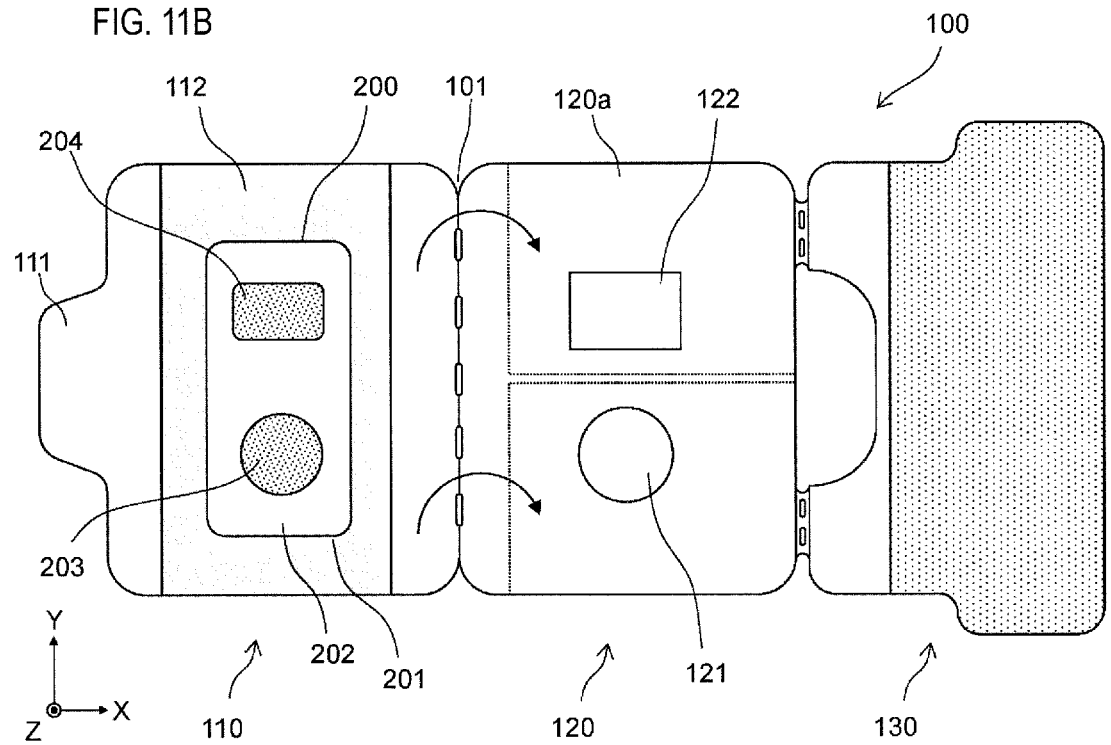
FIG. 11B is a plan view showing a process of unfolding the sheet when supporting the body fluid collection sheet on the support body according to the first embodiment.
Figure 12A:
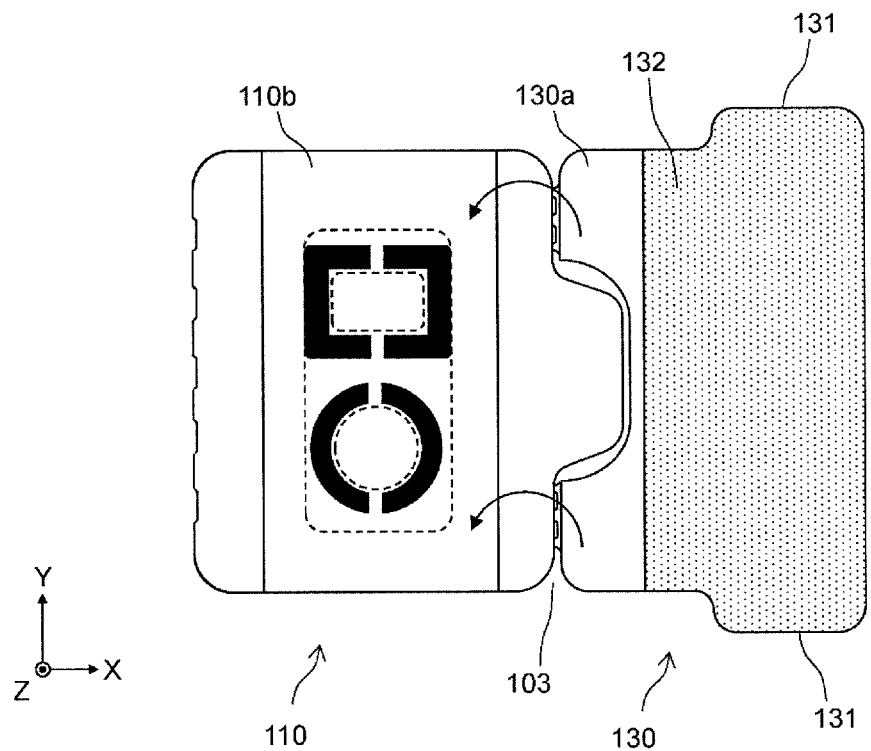
FIGS. 12A and 12B are plan views showing a folding process of a sheet when supporting the body fluid collection sheet on the support body according to the first embodiment.
Figure 12B:
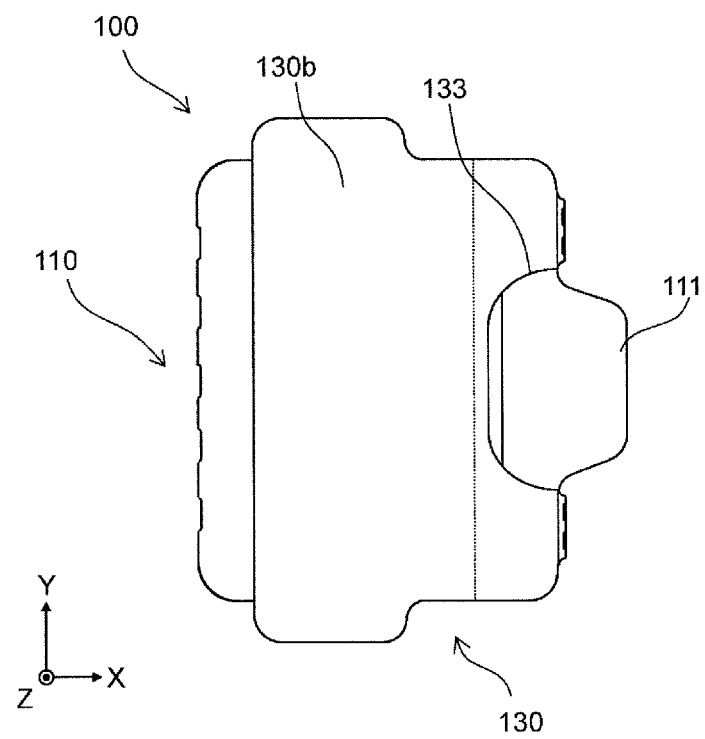

In this way, when the third sheet 130 is peeled off from the second sheet 120, the support body 100 is in the unfolded state shown in FIG. 11B. In this case, the back surface of the adhesive sheet 201 of the body fluid collection sheet 200 adheres to the adhesive surface 112 of the first sheet 110. The first body fluid collection body 203 and the second body fluid collection body 204 are exposed on the Z-axis positive side.

Returning to FIG. 8, in step S18, the operator folds the first sheet 110 onto the second sheet 120 and adheres the first sheet 110 to the second sheet 120. In step S19, the operator folds the third sheet 130 onto the first sheet 110 and adheres the third sheet 130 to the first sheet 110.

Specifically, in the state of FIG. 11B, the operator grips the flange part 111 of the first sheet 110 and folds the first sheet 110 on the top surface 120a of the second sheet 120. As a result, the first body fluid collection body 203 and the second body fluid collection body 204 on the first sheet 110 respectively enter the holes 121 and 122 of the second sheet 120. Thus, the support body 100 is in the state shown in FIG. 12A. Thereafter, the operator presses the bottom surface 110b of the first sheet 110 with a finger or the like, and securely adheres the adhesive surface 112 of the first sheet 110 to the top surface 120a of the second sheet 120. In this way, the body fluid collection sheet 200 is sealed and supported while being sandwiched between the first sheet 110 and the second sheet 120.

The area of the adhesive surface 112 of the first sheet 110 is larger than the area of the body fluid collection sheet 200. Therefore, the second sheet 120 can be appropriately adhered to the adhesive surface 112 of the first sheet 110 in a state in which the adhesive sheet 201 of the body fluid collection sheet 200 is adhered to the adhesive surface 112 of the first sheet 110.

The top surface 120a of the second sheet 120 is cleanly protected by the third sheet 130 until immediately before the adhesive surface 112 of the first sheet 110 is adhered. Accordingly, contamination of the first body fluid collecting body 203 and the second body fluid collecting body 204 can be reliably prevented.

The operator also grips the flange part 131 of the third seat 130 and folds the third seat 130 on the bottom face 110b of the first seat 110. In this way, the adhesive surface 132 formed on the top surface 130a of the third sheet 130 adheres to the bottom surface 110b of the first sheet 110. Thus, the support body 100 is in the state shown in FIG. 12B. The operator presses the bottom surface 130b of the third sheet 130 with a finger or the like, and securely adheres the adhesive surface 132 of the third sheet 130 to the bottom surface 110b of the first sheet 110.

In this way, it is possible to prevent the first sheet 110 from unexpectedly peeling off from the second sheet 120 by adhering the third sheet 130 to the bottom surface 110b of the first sheet 110. Therefore, the body fluid collection sheet 200 can be more reliably and stably supported by the support body 100.

As shown in FIG. 11B, the operator can easily remove the body fluid collection sheet 200 from the skin 400 using the first sheet 110 and thereafter fold the first sheet 110 onto the second sheet 120 and the first sheet 110 then can be adhered to the second sheet 120 in an overlapping manner.

As shown in FIG. 11B, holes 121 and 122 which configure receiving parts to accommodate the first body fluid collection body 203 and the second body fluid collection body 204 are provided on the top surface 120a of the second sheet 120 when the first sheet 110 is folded over the second sheet 120. Therefore, it is possible to prevent excessive pressure from being applied to the first body fluid collection body 203 and the second body fluid collecting body 204 when the first sheet 110 is folded over the second sheet 120. The first body fluid collection body 203 and the second body fluid collection body 204 therefore can be smoothly supported between the first sheet 110 and the second sheet 120.

Figure 13A:
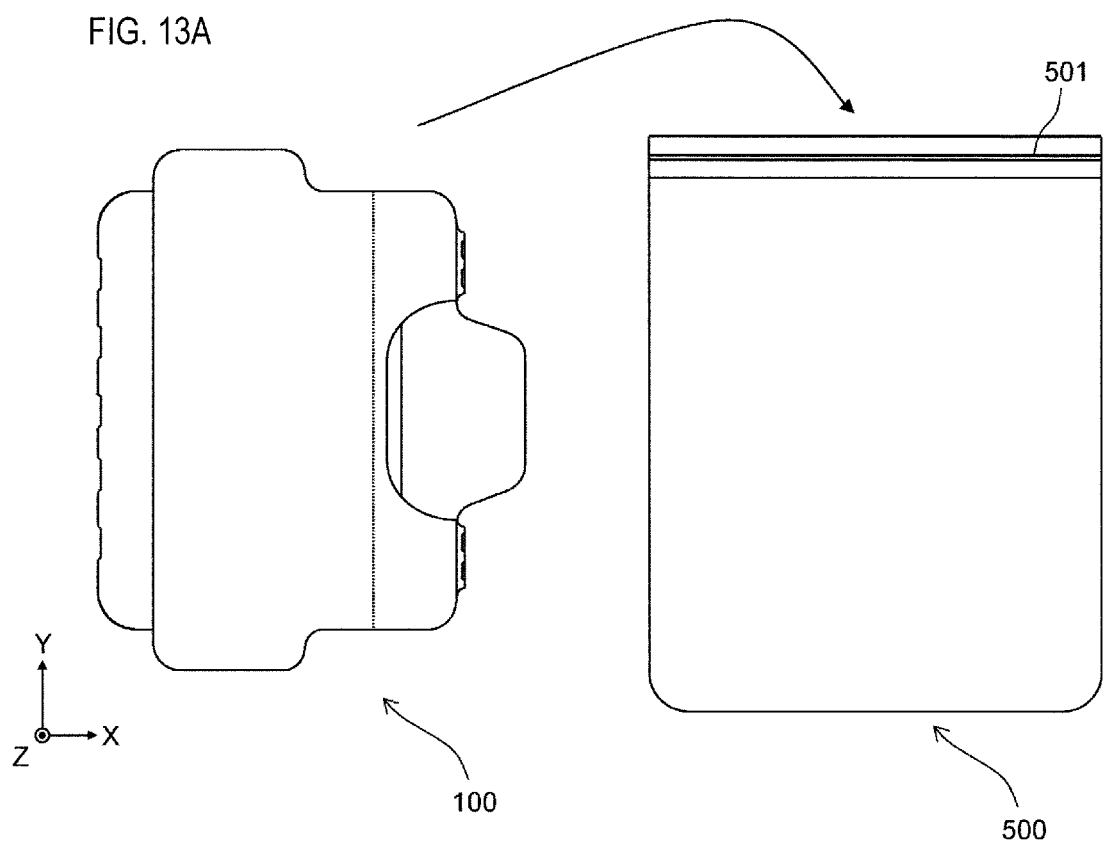
FIGS. 13A and 13B are plan views showing the process of placing the support body supporting the body fluid collection sheet in a bag according to first embodiment.
Figure 13B:
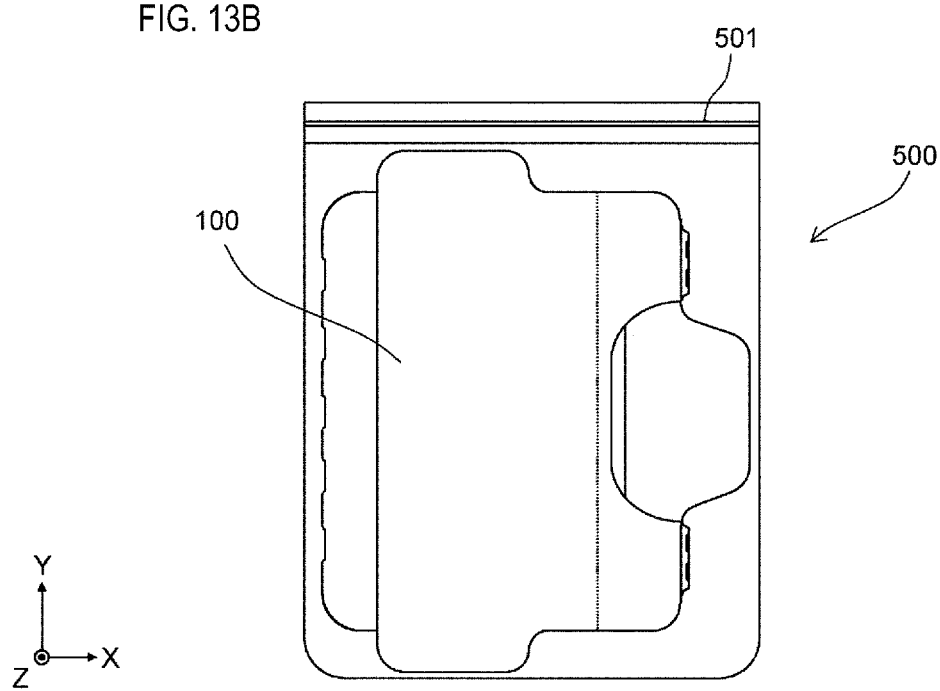

As shown in FIG. 13A, the support body 100 supporting the body fluid collection sheet 200 is suitably stored in a bag 500 the upper part of which is open. The bag 500 is provided with a seal part 501 for closing the upper part. As shown in FIG. 13B, the operator stores the support body 100 in the bag 500 from the upper part of the bag 500, and then closes the upper part of the bag 500 with the seal part 501. For the sake of convenience, FIG. 13B shows a state in which the inside of the bag 500 is visible. The bag 500 preferably is made of a material which is not easily damaged. Thereafter, the bag 500 is conveyed to a measuring facility or the like that measures the body fluid collection sheet 200.

Figure 14A:
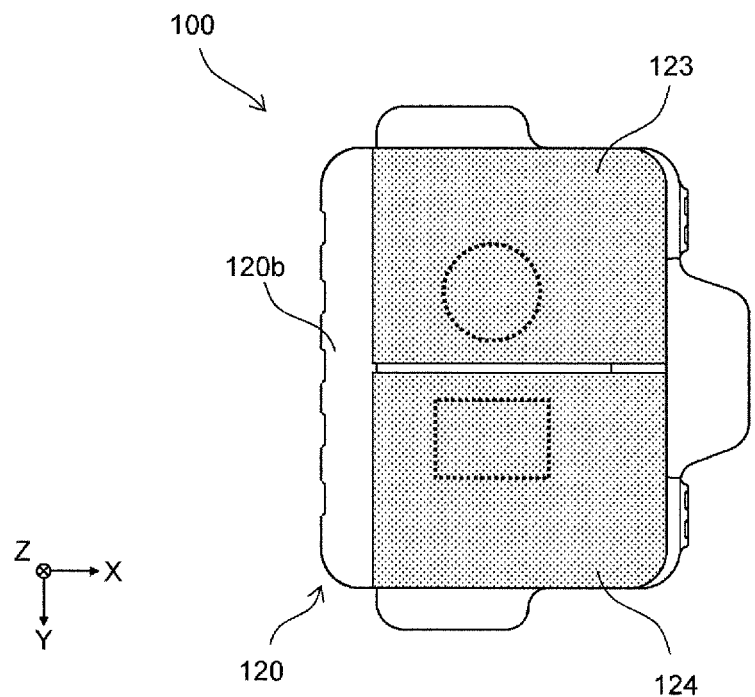
FIGS. 14A and 14B are plan views showing a peeling process of a peeling member when a support body supporting the body fluid collection sheet is subjected to measurement according to the first embodiment.
Figure 14B:
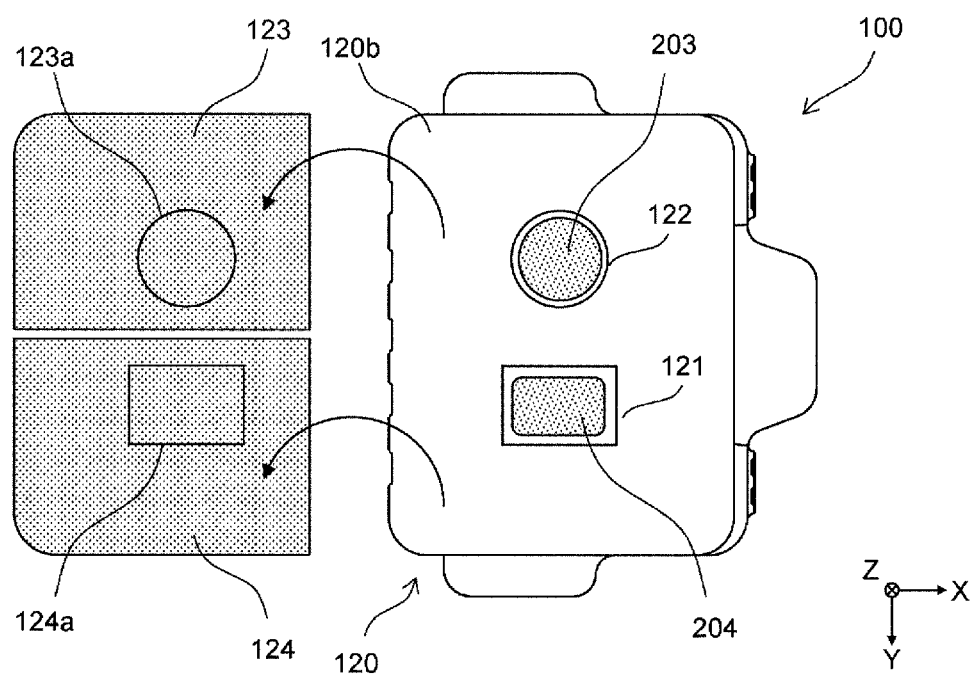

As shown in FIG. 14A, the measurer takes out the support body 100 from the bag 500 at the time of measurement. The measurer peels off the peeling members 123 and 124 from the bottom surface 120b of the second sheet 120. In this way, as shown in FIG. 14B, the first body fluid collection body 203 and the second body fluid collection body 204 are exposed through the holes 121 and 122 formed in the second sheet 120. The first body fluid collection body 203 and the second body fluid collection body 204 can be exposed to the outside for measurement by simple operations of peeling off the peeling members 123 and 124.

The measurer removes the first body fluid collection body 203 and the second body fluid collection body 204 with a jig such as tweezers and sets the first body fluid collection body 203 and the second body fluid collection body 204 in the measuring apparatus. In this way, the tissue fluid and perspiration collected in the first body fluid collection body 203 and the second body fluid collection body 204 are measured, and the blood glucose level of the patient is acquired.

The first body fluid collection body 203 and the second body fluid collection body 204 do not necessarily have to be detached from the support body 100. As shown in FIG. 14B, with the first body fluid collection body 203 and the second body fluid collection body 204 exposed, the support body 100 may be set as is in the measuring apparatus. In this case, for example, the measuring apparatus has a configuration that holds the surface of the support body 100 at the negative side of the Z-axis to stably hold the support body 100 at the measurement position.

Second Embodiment

Figure 15A:
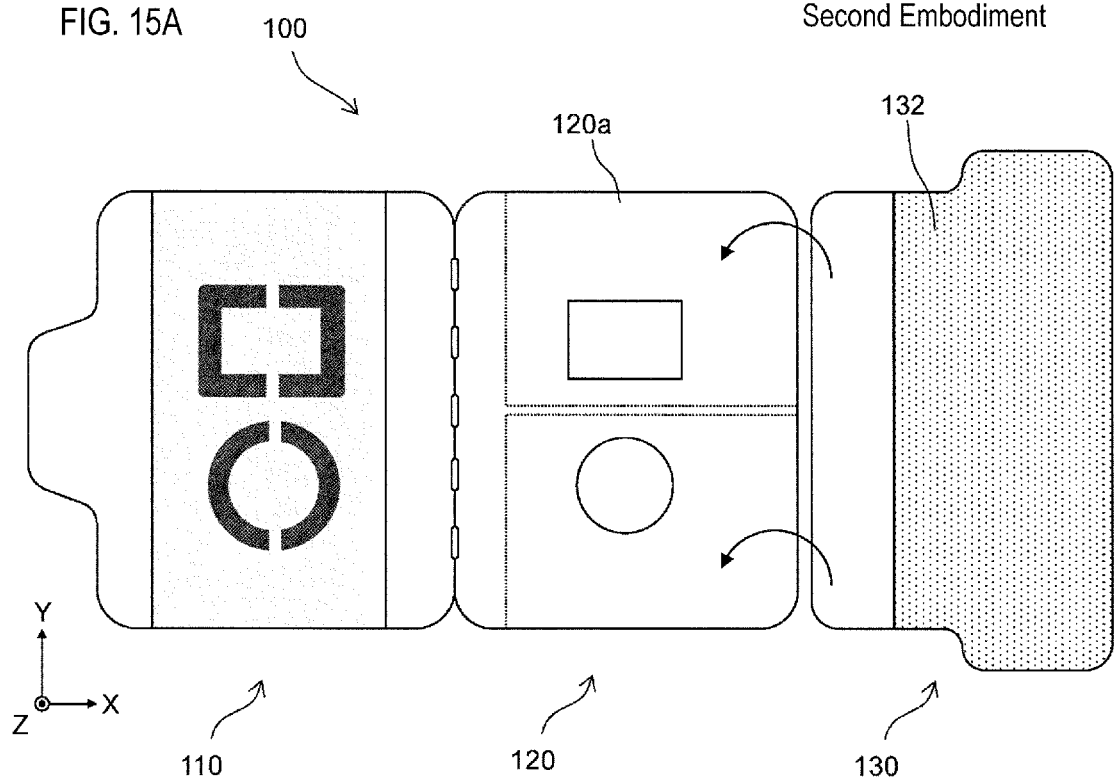
FIG. 15A is a plan view schematically showing a configuration of a support body according to a second embodiment.

As shown in FIG. 15A, in the second embodiment the third sheet 130 is separate from the second sheet 120. The notch 133 also is not formed in the third sheet 130. Other configurations of the support body 100 in the second embodiment are the same as those in the first embodiment.

Figure 15B:
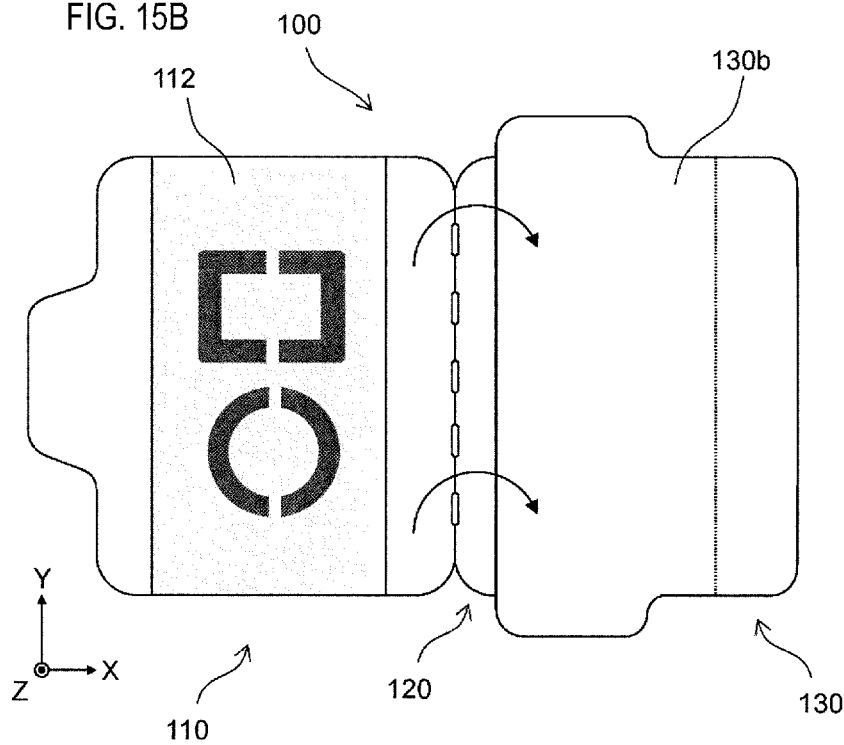
FIG. 15B is a plan view showing a folding process of each sheet in the case of producing the support body before use according to the second embodiment.

Before use, the third sheet 130 is stacked on the top surface of the second sheet 120 and adhered thereto. In this way, the support body 100 is in the state of FIG. 15B. As indicated by arrows in FIG. 15B, the first sheet 110 also is folded over the bottom surface of the third sheet 130. In this way, the support body 100 becomes the final form before use. The final form is the same as FIG. 5A, except that the third sheet 130 is not connected to the second sheet 120.

Figure 16A:
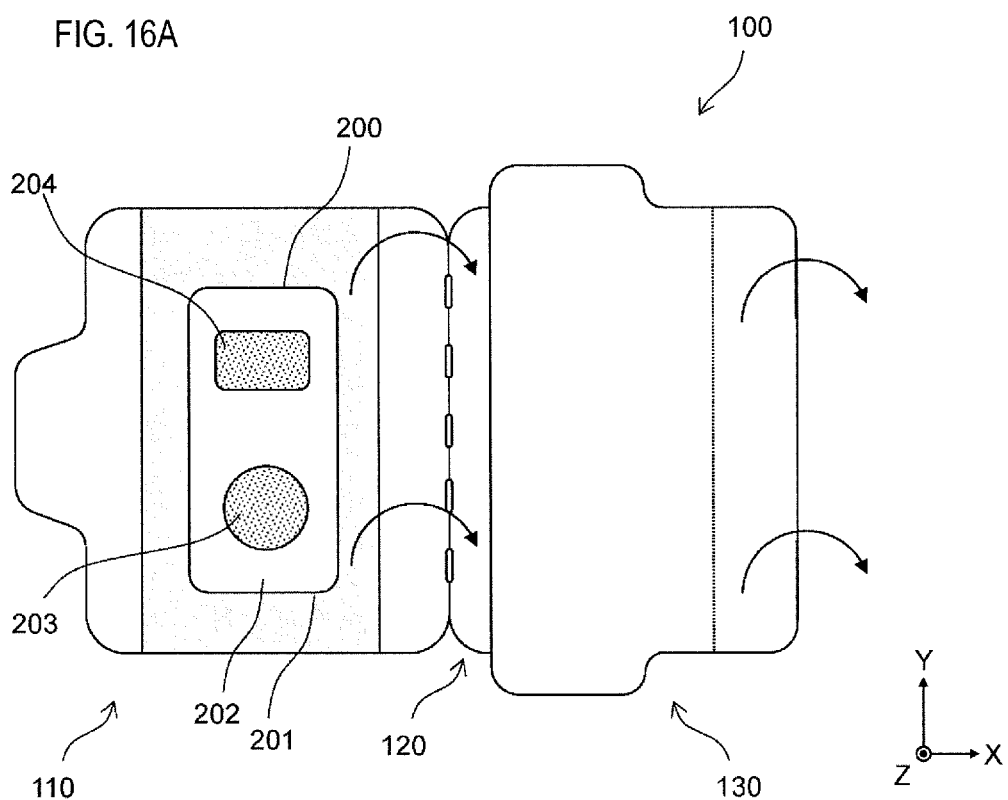
FIGS. 16A and 16B are plan views showing a folding process of a sheet when supporting a body fluid collection sheet on a support body according to the second embodiment.
Figure 16B:
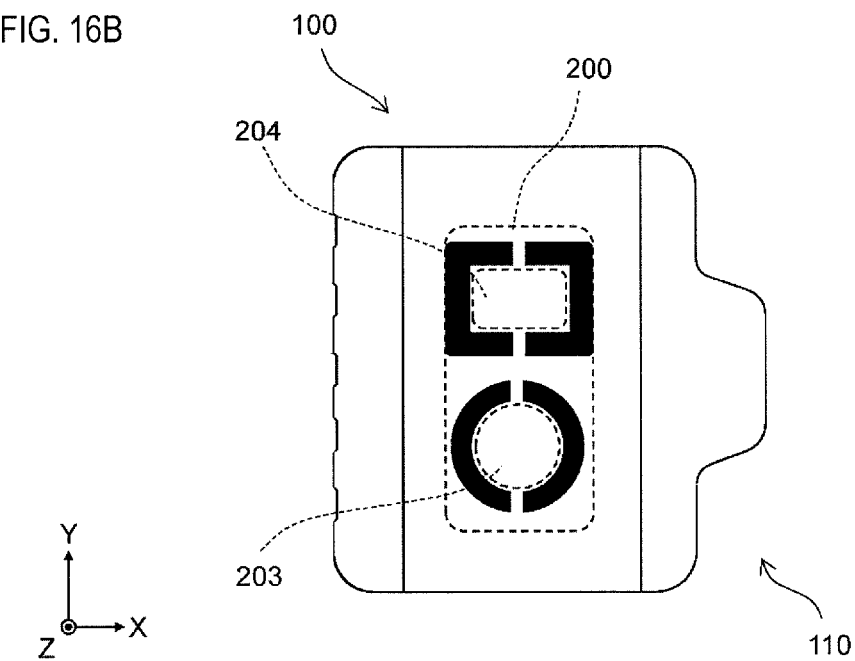
Figure 17A:
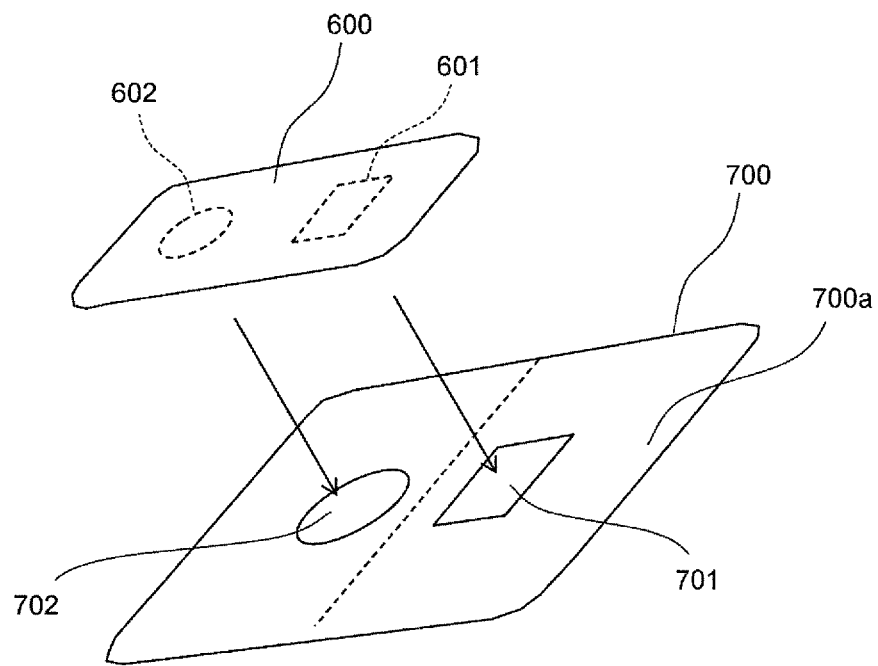
FIGS. 17A and 17B are diagrams showing a configuration of a support body described in Japanese Patent Application Publication No. 2014-143845.
Figure 17B:
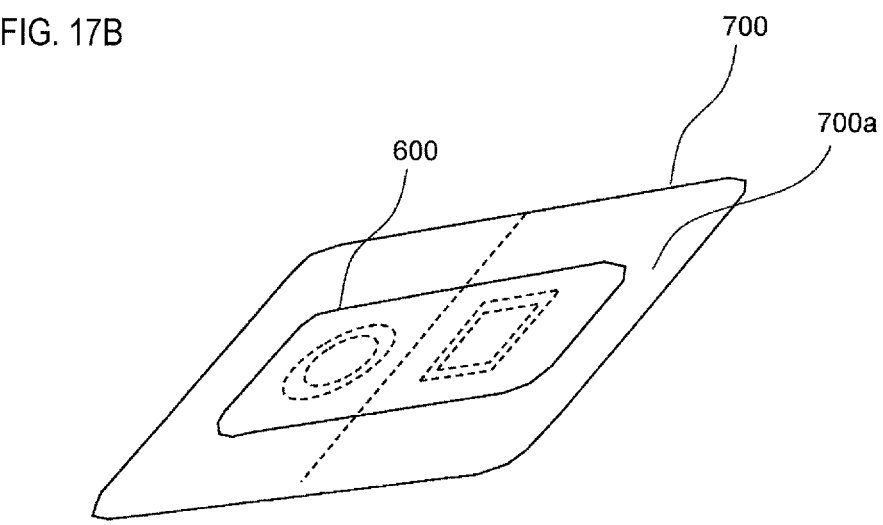

When using the support body 100, each sheet is unfolded in the same procedure as in the first embodiment. First, the first sheet 110 is unfolded, the body fluid collection sheet 200 is attached to the adhesive surface 112 of the first sheet 110, and the body fluid collection sheet 200 is peeled off from the skin 400. FIG. 16A shows the state at this time. The operator peels off the third sheet 130 from the second sheet 120. In the second embodiment, when the third sheet 130 is peeled off from the second sheet 120, the third sheet 130 is completely separated from the second sheet 120 since the third sheet 130 is not connected to the second sheet 120. The separated third sheet 130 is discarded. Next, the operator folds the first sheet 110 on the top surface 120a of the second sheet 120. In this way, as shown in FIG. 16B, the body fluid collection sheet 200 is sealed sandwiched and supported between the first sheet 110 and the second sheet 120, as shown in FIG. 16B.

Also according to the second embodiment, the body fluid collection sheet 200 can be supported on the support body 100 without contamination by a simple operation the same as the first embodiment. In the second embodiment, the third sheet 130 is not used for supporting the body fluid collection sheet 200. In contrast, in the first embodiment, the body fluid collection sheet 200 is supported together with the first sheet 110 and the second sheet 120 using the third sheet 130. Therefore, in the first embodiment, the body fluid collection sheet 200 can be more reliably supported.

What is claimed is:

1. A body fluid collection method for collecting a body fluid using a body fluid collection sheet for collecting a body fluid, comprising:
    a step of adhering the body fluid collection sheet to skin;
    a step of collecting the body fluid with the body fluid collection sheet after the step of adhering the body fluid collection sheet to skin;
    a step of adhering an adhesive surface of a first sheet of a support body to the body fluid collection sheet after the step of collecting the body fluid with the body fluid collection sheet;
    a step of separating the body fluid collection sheet from the skin by separating the support body adhered to the body fluid collection sheet from the skin after the step of adhering the adhesive surface of the first sheet of the support body to the body fluid collection sheet; and
    a step of overlaying a second sheet of the support body on the adhesive surface of the first sheet and supporting the body fluid collection sheet between the first sheet and the second sheet after the step of separating the body fluid collection sheet from the skin.

2. The method according to claim 1, wherein
    the body fluid collection sheet comprises a body fluid collection body that adheres to the skin and collects bodily fluids; and
    wherein in the second sheet, holes through the second sheet are provided in a region in which the body fluid collection body is positioned when overlaid on the first sheet are formed, and wherein the second sheet comprises a peeling member disposed peelably on a surface on a side opposite to a surface of the second sheet overlaid on the first sheet, such that the peeling member occludes the holes from the opposite surface.

3. The method according to claim 1, wherein the second sheet is integrally provided with the first sheet so as to foldably overlap with the adhesive surface.

4. The method of claim 3, wherein a notch is provided at a boundary of the first sheet and the second sheet.

5. The method according to claim 1, wherein an area of the adhesive surface of the first sheet is larger than an area of the body fluid collection sheet.

6. The method according to claim 1, wherein the body fluid collection sheet comprises:
a body fluid collection body that adheres to the skin and collects bodily fluids; and
the first sheet is formed to be transparent or semitransparent and comprises a marker indicating a region where the body fluid collecting sheet is to be positioned.

7. The method according to claim 1, wherein a third sheet is integrally formed on the second sheet and foldable with the second sheet.

8. The method of claim 7, wherein a notch is provided at a boundary of the second sheet and the third sheet.

9. The method according to claim 7, wherein the third sheet has an adhesive surface for adhering to the second sheet.

10. The method according to claim 9, wherein an adhesive strength of the adhesive surface of the third sheet is weaker than an adhesive strength of the adhesive surface of the first sheet.

11. The method according to claim 9, wherein a surface of the third sheet on an opposite side to the adhesive surface of the third sheet is a non-adhesive surface.

12. The method according to claim 7, wherein in a pre-use state, the third sheet is folded over the second sheet, and the first sheet is folded over the third sheet.

13. The method according to claim 12, wherein the first sheet is configured to have a flange part protruding from a side edge of a contour of the third sheet and the second sheet in a state in which the adhesive surface of the first sheet is overlaid and adhered to a surface of the third sheet on an opposite side to an adhesive surface of the third sheet.

14. The method according to claim 12, wherein the third sheet comprises a flange part protruding from a side edge of the second sheet in a state in which the third sheet is overlaid and adhered to the second sheet.

* * * * *